(12) United States Patent
Kataoka et al.

(10) Patent No.: US 8,961,949 B2
(45) Date of Patent: Feb. 24, 2015

(54) POLYMER-METAL COMPLEX COMPOSITE HAVING MRI CONTRAST ABILITY AND MRI CONTRASTING AND/OR ANTITUMOR COMPOSITION USING THE SAME

(75) Inventors: Kazunori Kataoka, Tokyo (JP); Sachiko Kaida, Osaka (JP); Horacio Cabral, Tokyo (JP); Michiaki Kumagai, Saitama (JP); Masaki Sekino, Tokyo (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 561 days.

(21) Appl. No.: 13/000,836

(22) PCT Filed: Jun. 26, 2009

(86) PCT No.: PCT/JP2009/061772
§ 371 (c)(1), (2), (4) Date: Feb. 3, 2011

(87) PCT Pub. No.: WO2009/157561
PCT Pub. Date: Dec. 30, 2009

(65) Prior Publication Data
US 2011/0123458 A1    May 26, 2011

(30) Foreign Application Priority Data
Jun. 26, 2008 (JP) .................... 2008-167823

(51) Int. Cl.
| *A61K 31/74* | (2006.01) |
| *C08G 83/00* | (2006.01) |
| *A61K 47/48* | (2006.01) |
| *A61K 49/14* | (2006.01) |
| *A61K 49/12* | (2006.01) |

(52) U.S. Cl.
CPC ........ *A61K 47/48315* (2013.01); *C08G 83/001* (2013.01); *A61K 47/48215* (2013.01); *A61K 49/146* (2013.01); *A61K 49/128* (2013.01)

USPC ..... 424/78.37; 424/1.21; 424/1.29; 424/1.33; 424/1.37; 424/1.65; 424/9.34; 424/9.364; 424/9.365

(58) Field of Classification Search
None
See application file for complete search history.

(56) References Cited

U.S. PATENT DOCUMENTS

| 5,420,319 | A | 5/1995 | Okamoto et al. | |
| 2002/0197261 | A1* | 12/2002 | Li et al. ...................... | 424/178.1 |
| 2003/0170201 | A1 | 9/2003 | Kataoka et al. | |
| 2007/0148125 | A1* | 6/2007 | Kataoka et al. ............ | 424/78.27 |
| 2008/0241073 | A1 | 10/2008 | Yokoyama et al. | |
| 2009/0082438 | A1* | 3/2009 | Kataoka et al. ............... | 514/492 |

FOREIGN PATENT DOCUMENTS

| JP | 06-271593 | A | 9/1994 |
| JP | 06-329692 | A | 11/1994 |
| JP | 3955992 | B2 | 8/2007 |
| JP | 2008-167823 | A | 7/2008 |
| JP | 2008-222804 | A | 9/2008 |
| WO | WO-02/26241 | A1 | 4/2002 |
| WO | WO-03/017923 | A2 | 3/2003 |
| WO | WO-2006/003731 | A1 | 1/2006 |
| WO | WO 2006098496 | A1 * | 9/2006 |

* cited by examiner

*Primary Examiner* — James Rogers
(74) *Attorney, Agent, or Firm* — Dickstein Shapiro LLP

(57) ABSTRACT

The present invention provides a polymer-metal complex composite, which comprises a block copolymer capable of serving as a constituent member of a polymeric micelle and a metal complex having MRI contrast ability, accumulates in a tumor-specific manner, achieves high image contrast even in a small amount, and has reduced side effects and a long retention time in blood.

The polymer-metal complex composite of the present invention comprises a block copolymer (A) represented by general formula (a) and a metal complex (B) having MRI contrast ability, wherein the composite comprises a structure in which a carboxyl anion of poly(carbo) in the copolymer (A) is attached to the metal complex (B) via a metal atom (M).

9 Claims, 15 Drawing Sheets

US 8,961,949 B2

POLYMER-METAL COMPLEX COMPOSITE HAVING MRI CONTRAST ABILITY AND MRI CONTRASTING AND/OR ANTITUMOR COMPOSITION USING THE SAME

TECHNICAL FIELD

The present invention relates to a composite comprising a block copolymer and a metal complex having MRI contrast ability, and an MRI contrasting composition comprising such a composite.

BACKGROUND ART

Under circumstances where the accumulated incidence rate and mortality of cancer keep on increasing, it is a challenge to detect cancer in its early stages at every site. If cancer is detected in its early stages, the risk of invasion during therapy can be reduced and it is also expected that the cancer can be cured completely. Protocols for early therapy have been established for each cancer, and hence there is a demand for simple techniques having high diagnostic ability. Moreover, in the case of a patient who has been diagnosed as having advanced cancer, accurately diagnosing the presence or absence of distant metastasis is very important for determination of the patient's disease stage and the therapeutic strategy required subsequently. Cancer therapies include surgical operations, radiotherapy and chemotherapy. In the case of surgical operations, it is expected that cancer can be cured completely when metastasis lesions are precisely excised or cauterized. Radiation therapy also allows reduction of side effects when tumor sites are precisely determined and selectively irradiated to thereby avoid irradiation in other normal sites. In these senses, accurate diagnosis of cancer sites is very advantageous for cancer patients at all stages of the disease.

Diagnostic imaging of malignant tumors is typically exemplified by X-ray CT imaging, ultrasonic echo imaging, and magnetic resonance imaging (MRI). These diagnoses are widely used and each have both advantages and disadvantages. Among them, MRI is advantageous in that it requires no exposure to radiation and is a highly objective and reproducible method. However, it has been difficult for MRI to identify small tumors by its hardware alone.

To compensate such a disadvantage, various contrast agents have been developed and practically used for enhancing contrast between tumor tissues and their surrounding tissues. Typical contrast agents include metal complexes such as Gd-DTPA (gadolinium-diethylene triamine pentaacetic acid), which has side effects such as hepatotoxicity and nephrotoxicity although Gd-DTPA is in a chelated form with reduced side effects compared to free Gd. Moreover, Gd-DTPA is not site-specific and is rapidly diffused into individual organs and muscle tissues upon intravenous injection. Thus, there has been a limit on the time required between administration and imaging, and it has also been necessary to administer a large amount of contrast agent to ensure clear contrast between tumors and non-tumor tissues.

For these reasons, there is a demand for the development of a contrast agent which accumulates in a tumor-specific manner, achieves high contrast even in a small amount, is safe with reduced side effects, and also has a long retention time in blood.

In tumor tissues, due to their properties different from those of normal tissues, e.g., neovascular outgrowth and highly enhanced permeability of vascular walls, as well as undeveloped lymphatic system, even high-molecular-weight substances can be transferred from blood to tumor tissues and are less likely to be excreted from the tissues once they have been transferred. It is therefore known that nano-size particles such as liposomes or polymeric micelles encapsulating various agents (e.g., anticancer agents) eventually accumulate in tumor tissues, as a result of the so-called EPR effect, which facilitates accumulation of high-molecular-weight compounds and/or nano-size particles in tumor tissues (see Patent Document 1).

On the other hand, polymeric micelles encapsulating a Gd complex in the core have been developed so far (see Patent Document 2). However, in these micelles, the Gd complex is directly attached and immobilized to a block copolymer constituting the micelles, as a result of which the relaxivity (contrast agent sensitivity) of Gd is suppressed and Gd is less likely to be excreted from tumor tissues. Thus, there has been a concern about problems of side effects such as hepatotoxicity and nephrotoxicity.

PRIOR ART DOCUMENTS

Patent Documents

[Patent Document 1] Japanese Patent No. 3955992
[Patent Document 2] International Publication No. WO2006/003731

DISCLOSURE OF THE INVENTION

Problems to be Solved by the Invention

A problem to be solved by the present invention is to provide a polymer-metal complex composite which comprises a block copolymer capable of serving as a constituent member of a polymeric micelle and a metal complex having MRI contrast ability, wherein the composite accumulates in a tumor-specific manner, achieves high image contrast even in a small amount, and has reduced side effects and a long retention time in blood.

Another problem to be solved by the present invention is to provide an MRI contrasting (and/or antitumor) composition or kit which comprises such a composite, as well as an MRI contrasting method for tumor detection which uses such a composite.

Means for Solving the Problems

The inventors of the present invention have made extensive and intensive efforts to solve the above problems. As a result, the inventors have found that the above problems can be solved when a block copolymer capable of serving as a constituent member of a polymeric micelle is attached to a metal complex having MRI contrast ability via another metal complex or a metal atom. This finding led to the completion of the present invention. Moreover, for example, if a metal complex having antitumor activity is used as another metal complex as described above, the resulting composite can be used not only as an MRI contrasting composition, but also as an antitumor composition (pharmaceutical composition).

Namely, the present invention is as follows.
(1) A polymer-metal complex composite, which comprises a block copolymer (A) represented by the following general formula (a) and a metal complex (B) having MRI contrast ability:

poly(hph)-block-poly(carbo)     (a)

[wherein poly(hph) represents an uncharged hydrophilic polymer chain segment, and poly(carbo) represents a polymer chain segment having carboxyl groups in its side chain]

wherein the composite comprises a structure in which a carboxyl anion of poly(carbo) in the copolymer (A) is attached to the metal complex (B) via a metal atom (M).

Examples of the composite according to (1) above include those comprising a structure in which a metal atom (M) is attached to a carboxyl anion of poly(carbo) in the copolymer (A), and the metal complex (B) is attached to the metal atom (M).

Examples of the composite according to (1) above include those in which poly(hph) is derived from a hydrophilic polymer selected from the group consisting of, for example, polyethylene glycol, poly(2-methyl-2-oxazoline), poly(2-ethyl-2-oxazoline), poly(2-isopropyl-2-oxazoline), polyacrylamide, polymethacrylamide, polyvinyl alcohol, poly(hydroxyethyl acrylate) and poly(hydroxyethyl methacrylate), as well as those in which poly(carbo) is derived from an anionic polymer selected from the group consisting of, for example, poly(glutamic acid), poly(aspartic acid), poly(acrylic acid), poly(methacrylic acid) and poly(malic acid).

Examples of the composite according to (1) above include those in which the metal atom (M) is, for example, a central metal atom in a metal complex. Examples of such a metal complex include a metal complex (C) having antitumor activity. In this case, the metal complex (C) may be, for example, immobilized to the block copolymer (A).

Specific examples of the composite according to (1) above include those represented by the following general formula (1) or (2).

[Chemical formula 1]

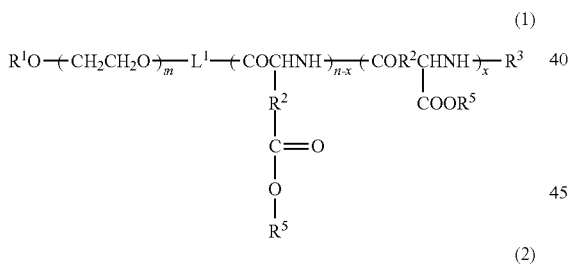

[wherein $R^1$ represents a hydrogen atom or an unsubstituted or substituted linear or branched $C_{1-12}$ alkyl group, $L^1$ and $L^2$ each represent a linker group, $R^2$ independently represents a methylene group or an ethylene group, $R^3$ independently represents a hydrogen atom, a protecting group for an amino group, a hydrophobic group or a polymerizable group, $R^4$ represents a hydroxyl group or an initiator residue, $R^5$ independently represents a hydrogen atom, an alkali metal ion, or a group represented by the following general formula (3) or (4):

[Chemical formula 2]

(wherein $R^6$ represents a metal atom or a group derived from a metal complex, and $R^7$ represents a group derived from a metal complex having MRI contrast ability)
(provided that $R^5$ comprises, at least in part, the group represented by general formula (3)), m represents an integer of 5 to 20,000, n represents an integer of 2 to 5,000, and x represents an integer of 0 to 5,000 (provided that $x \leq n$)]

Moreover, other specific examples of the composite according to (1) above include those represented by the following general formula (1-a) or (2-a).

[Chemical formula 3]

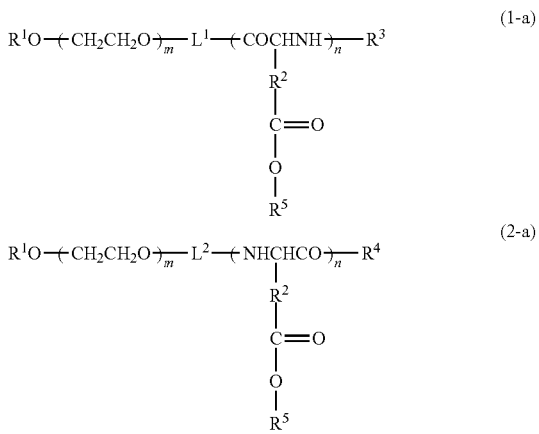

[wherein $R^1$ represents a hydrogen atom or an unsubstituted or substituted linear or branched $C_{1-12}$ alkyl group, $L^1$ and $L^2$ each represent a linker group, $R^2$ independently represents a methylene group or an ethylene group, $R^3$ independently represents a hydrogen atom, a protecting group for an amino group, a hydrophobic group or a polymerizable group, $R^4$ represents a hydroxyl group or an initiator residue, $R^5$ independently represents a hydrogen atom, an alkali metal ion, or a group represented by the following general formula (3) or (4):

[Chemical formula 4]

(wherein $R^6$ represents a metal atom or a group derived from a metal complex, and $R^7$ represents a group derived from a metal complex having MRI contrast ability)

(provided that $R^5$ comprises, at least in part, the group represented by general formula (3)), m represents an integer of 5 to 20,000, and n represents an integer of 2 to 5,000]

In the above general formulae (1), (2), (1-a) and (2-a), for example, $R^6$ may independently be a metal atom selected from platinum, copper, gold or iron, or may independently be a group derived from a metal complex having platinum, copper, gold or iron as a central metal atom. In the latter case, $R^6$ is exemplified, for example, by a group represented by the following general formula (5) or (6).

[Chemical formula 5]

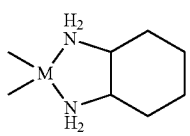

(5)

(6)

[wherein M represents a metal atom selected from platinum, copper, gold or iron]

Alternatively, $R^6$ may also be, for example, a group derived from a metal complex having antitumor activity, as specifically exemplified by a group represented by the following formula (5-a) or (6-a).

[Chemical formula 6]

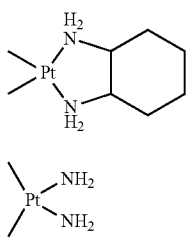

(5-a)

(6-a)

Moreover, in the above general formulae (1), (2), (1-a) and (2-a), for example, $R^7$ may independently be a group derived from a metal complex having gadolinium, europium, manganese, iron or copper as a central metal atom. In this case, examples of such a metal complex include metal complexes with multidentate ligands, and examples of multidentate ligands include aminocarboxylic acid or phosphoric acid compounds, porphyrin compounds, or deferrioxamine B. Among these compounds, aminocarboxylic acid or phosphoric acid compounds include, for example, ethylene diamine tetraacetic acid, diethylene triamine pentaacetic acid, diethylene triamine pentaacetic acid bismethylamide, triethylene tetramine hexaacetic acid, benzyloxypropionic pentaacetic acid, ethylene glycol tetramine tetraacetic acid, tetraazacyclododecane tetraacetic acid, tetraazacyclododecane triacetic acid, dihydroxyhydroxymethylpropyltetraazacyclododecane triacetic acid, hydroxypropyltetraazacyclododecane triacetic acid, or tetraazacyclododecane tetraphosphoric acid.

Specific examples of $R^7$ include groups represented by the following general formulae (7), (8), (9) and (10), and more specific examples include groups represented by the following formulae (7-a), (8-a), (9-a) and (10-a).

[Chemical formula 7]

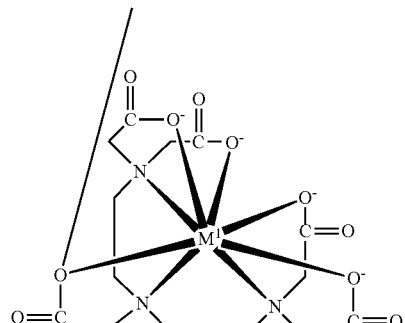

(7)

[Chemical formula 8]

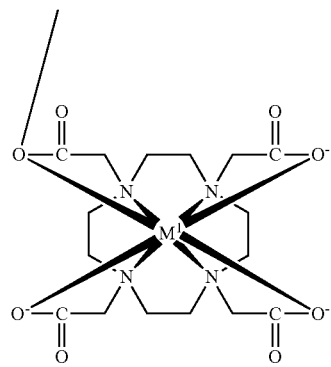

(8)

[Chemical formula 9]

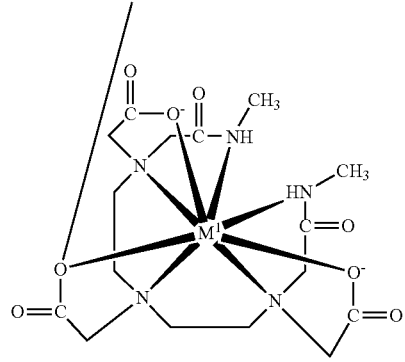

(9)

[Chemical formula 10]

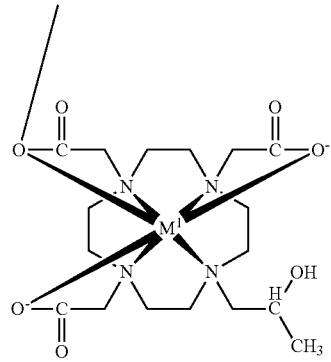

(10)

[wherein M¹ represents a metal atom selected from gadolinium, europium, manganese, iron or copper]

[Chemical formula 11]

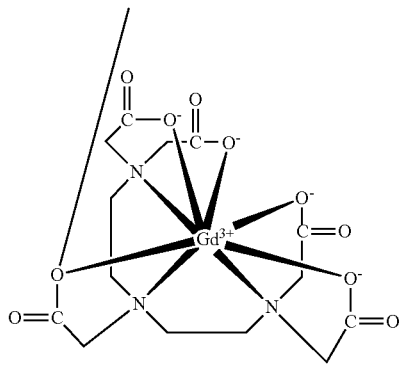

(7-a)

[Chemical formula 12]

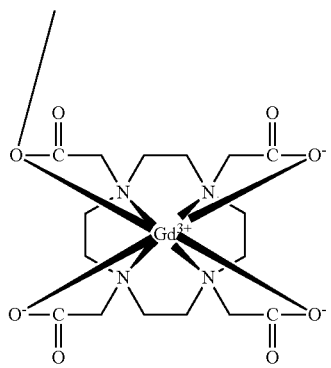

(8-a)

[Chemical formula 13]

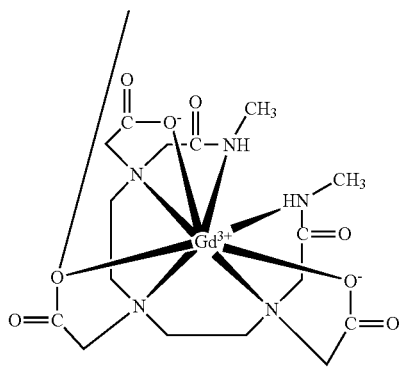

(9-a)

[Chemical formula 14]

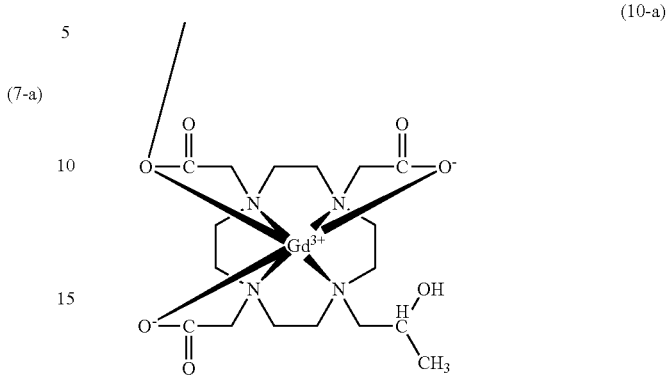

(10-a)

Moreover, in the above general formulae (1), (2), (1-a) and (2-a), for example, the group represented by general formula (3) shown above may independently be a group represented by the following general formula (11), (12), (13), (14), (15), (16), (17) or (18), and more specifically a group represented by the following formula (11-a), (12-a), (13-a), (14-a), (15-a), (16-a), (17-a) or (18-a).

[Chemical formula 15]

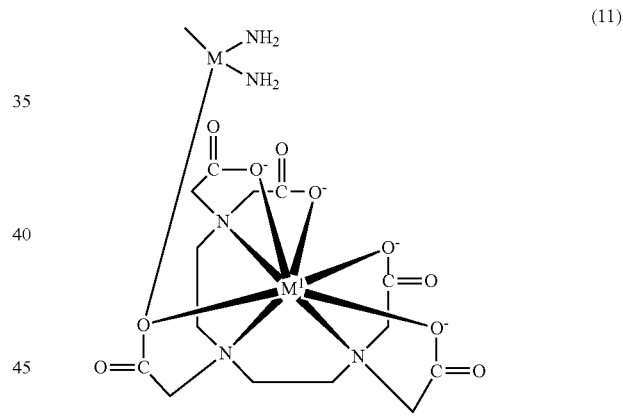

(11)

[Chemical formula 16]

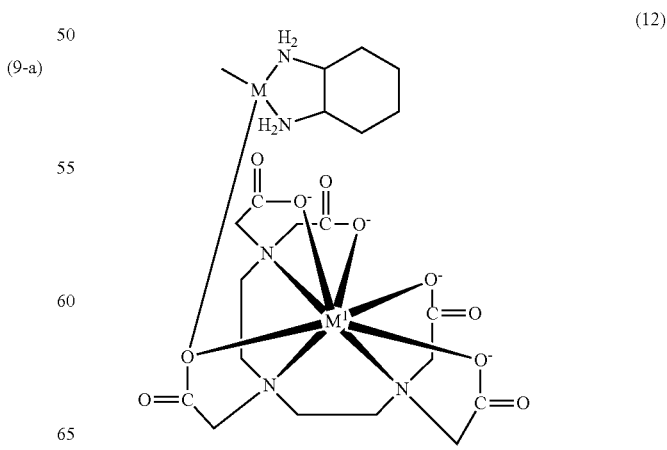

(12)

[Chemical formula 17]
(13)
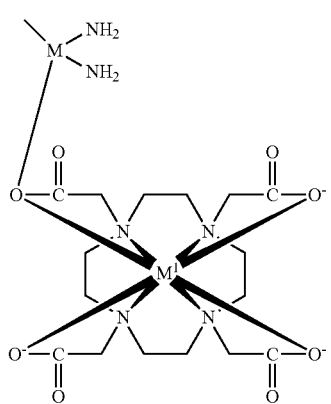
[Chemical formula 18]
(14)
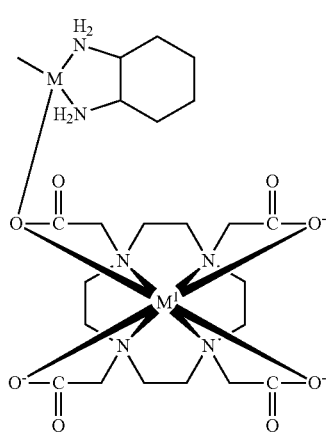
[Chemical formula 19]
(15)
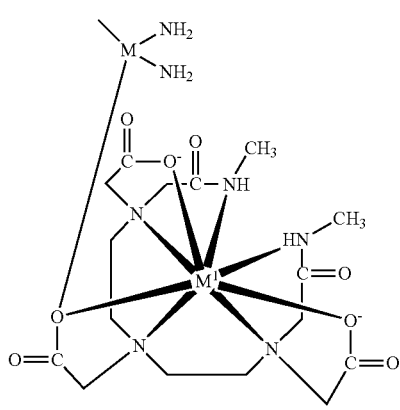
[Chemical formula 20]
(16)
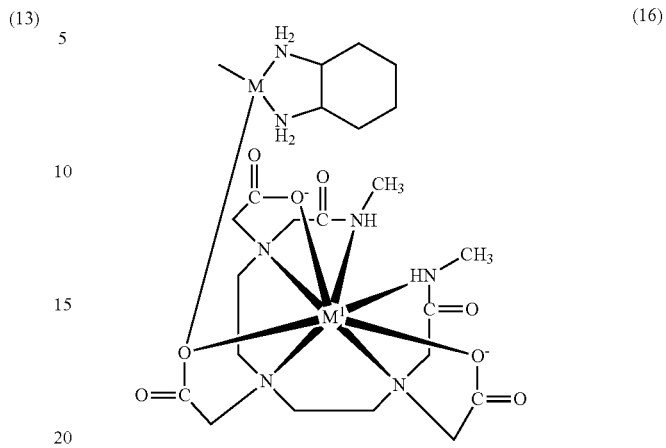
[Chemical formula 21]
(17)
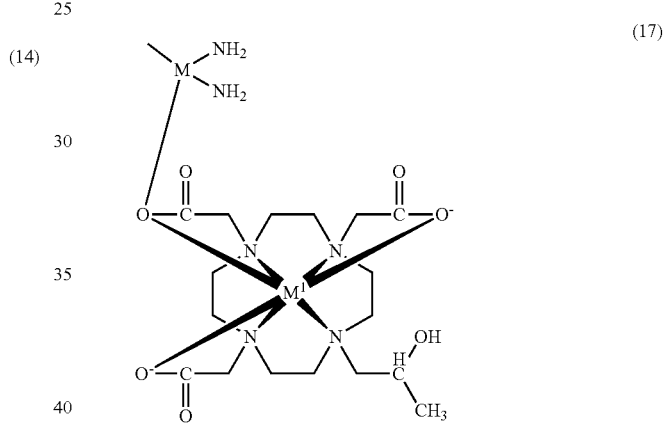
[Chemical formula 22]
(18)
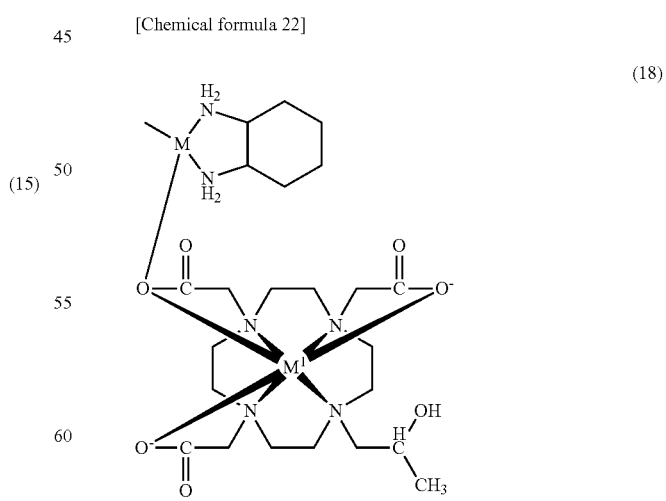
[wherein $M^1$ represents a metal atom selected from platinum, copper, gold or iron, or $M^1$ represents a metal atom selected from gadolinium, europium, manganese, iron or copper]

[Chemical formula 23]
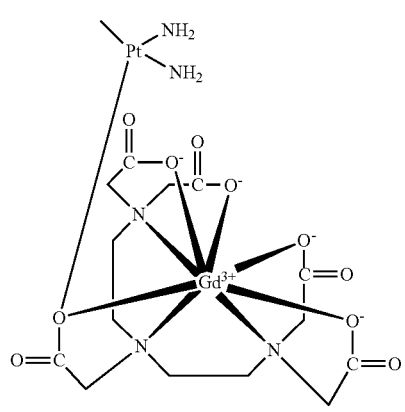
(11-a)
[Chemical formula 24]
(12-a)
[Chemical formula 25]
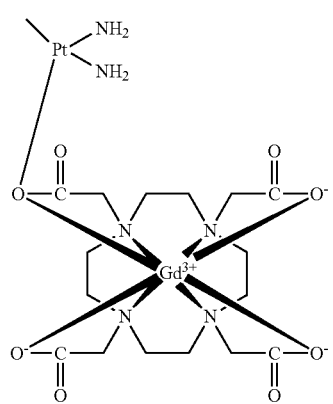
(13-a)
[Chemical formula 26]
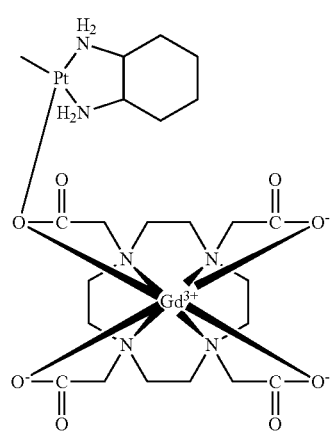
(14-a)
[Chemical formula 27]
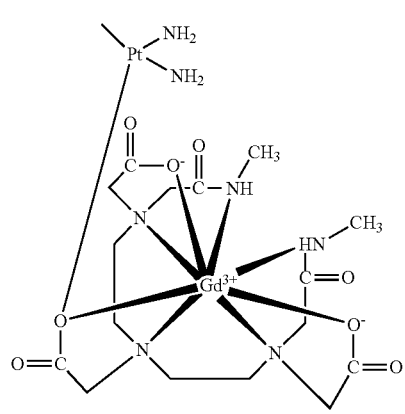
(15-a)
[Chemical formula 28]
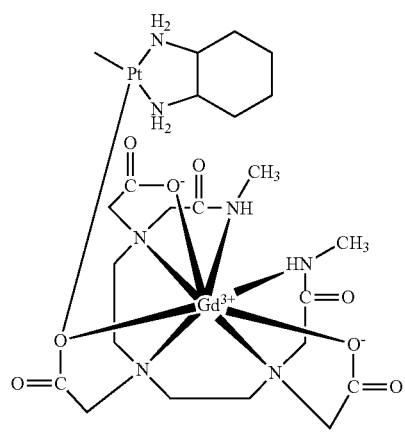
(16-a)

13

-continued

[Chemical formula 29]

(17-a)

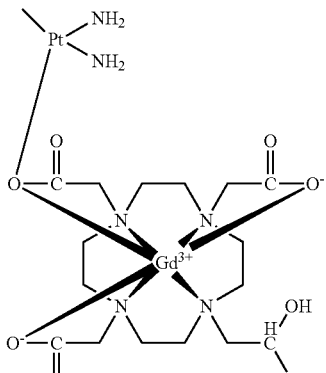

[Chemical formula 30]

(18-a)

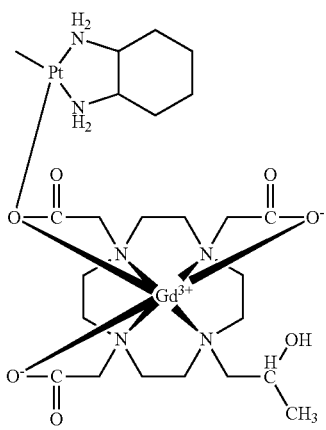

Examples of the composite according to (1) above include those encapsulating the metal complex having MRI contrast ability within micellar particles whose shell and core are formed by the above poly(hph) and poly(carbo) segments, respectively, as well as those further encapsulating a metal complex having antitumor activity. Composites in these forms are intended to mean aggregates in which multiple molecules of the composite according to (1) above are aggregated to form so-called polymeric micelles, and examples include those having an average dispersed particle size of 10 nm to 1 μm in an aqueous medium, as measured by dynamic light scattering.

(2) An MRI contrasting and/or antitumor composition, which comprises the composite according to (1) above.
(3) An MRI contrasting method for tumor detection, which comprises administering the composite according to (1) above to the body of an animal subject.
(4) An MRI contrasting and/or antitumor kit, which comprises the composite according to (1) above.

Advantageous Effect of the Invention

The present invention enables the provision of a polymer-metal complex composite which comprises a block copolymer capable of serving as a constituent member of a polymeric micelle and a metal complex having MRI contrast ability, wherein the composite accumulates in a tumor-specific manner, achieves high image contrast even in a small amount, and has reduced side effects and a long retention time in blood. The present invention further enables the provision of an MRI contrasting (and/or antitumor) composition or kit which comprises such a composite, as well as an MRI contrasting method for tumor detection which uses such a composite.

About 20% of Gd was found to be accumulated within tumor at 22 hours after injection, while Gd and Pt were each detected at a content of 10% in plasma after 22 hours, indicating that their retention in blood was high.

Figure 10:
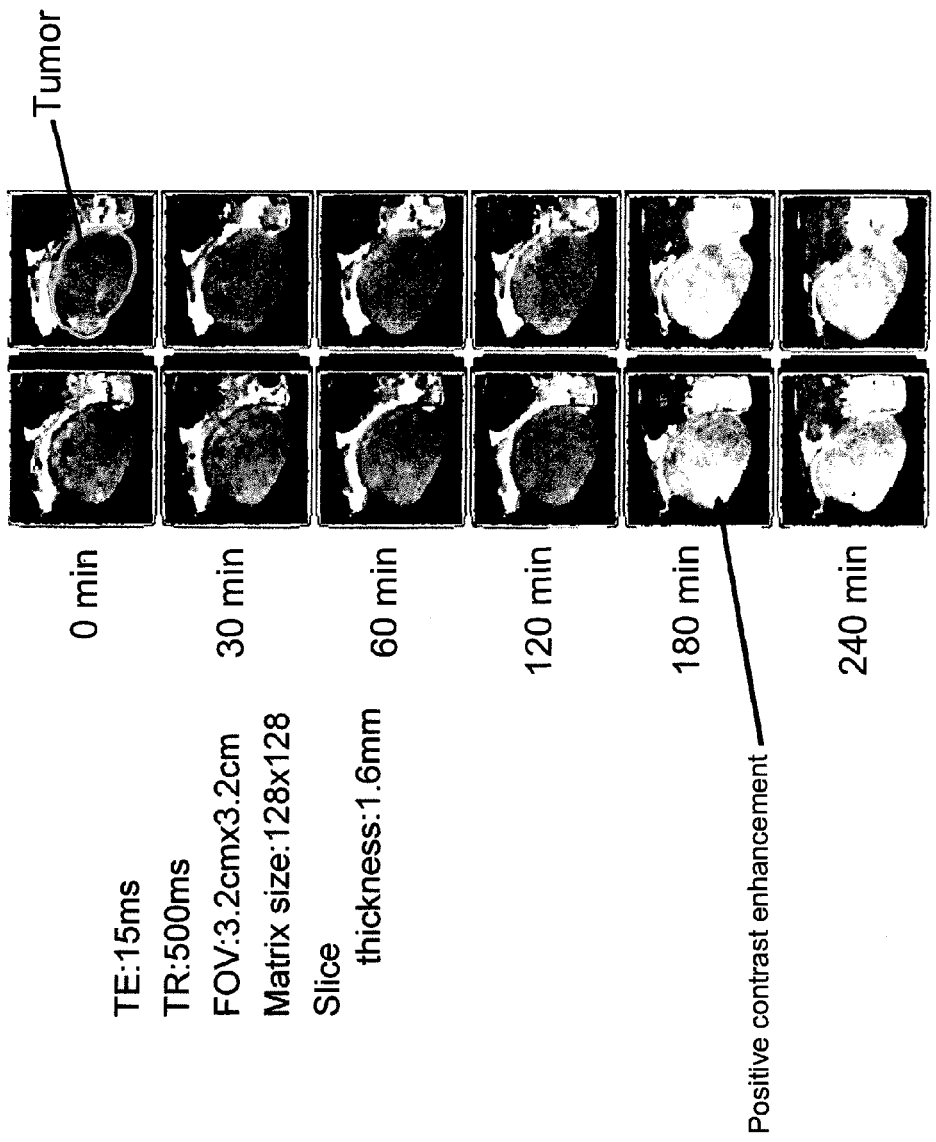

FIG. 10 presents MRI images showing the results of in vivo MRI experiment. This figure shows two slices including the center of tumor. A positive contrast enhancement was found to appear at 30 minutes after micelle administration, and reached a maximum after 180 and 240 minutes.

Figure 11:
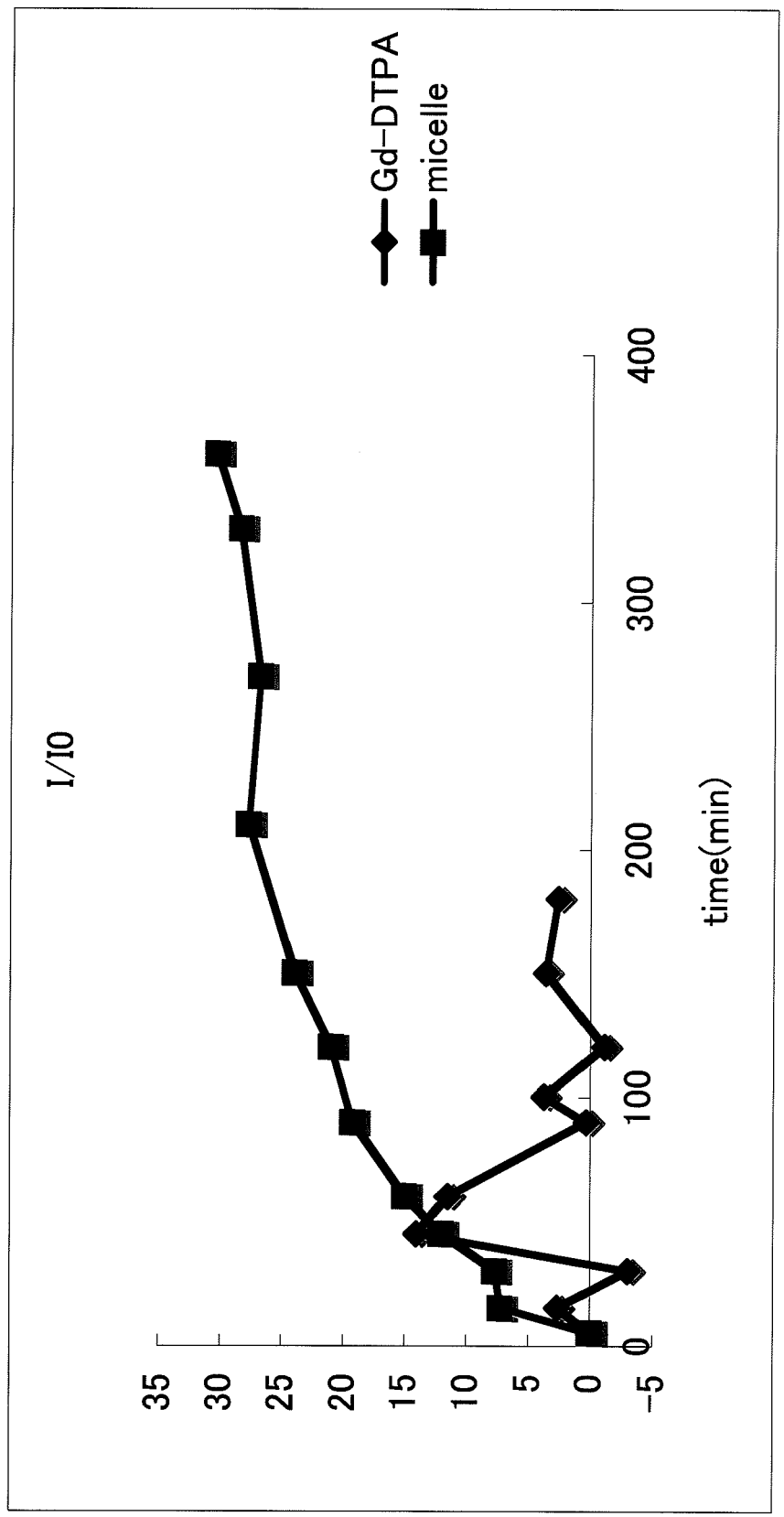

FIG. 11 is a graph showing the results of contrast enhancement in tumor, compared between free Gd-DTPA and Gd-DTPA/DACHPt-encapsulating micelles. In the graph, the vertical axis I/I0 represents an increase (%) in signal intensity after micelle administration, relative to the signal intensity in tumor before micelle administration. When compared to Gd- DTPA, the micelles were found to have a higher contrast enhancement and to maintain their contrast enhancement for at least 6 hours.

Figure 12:
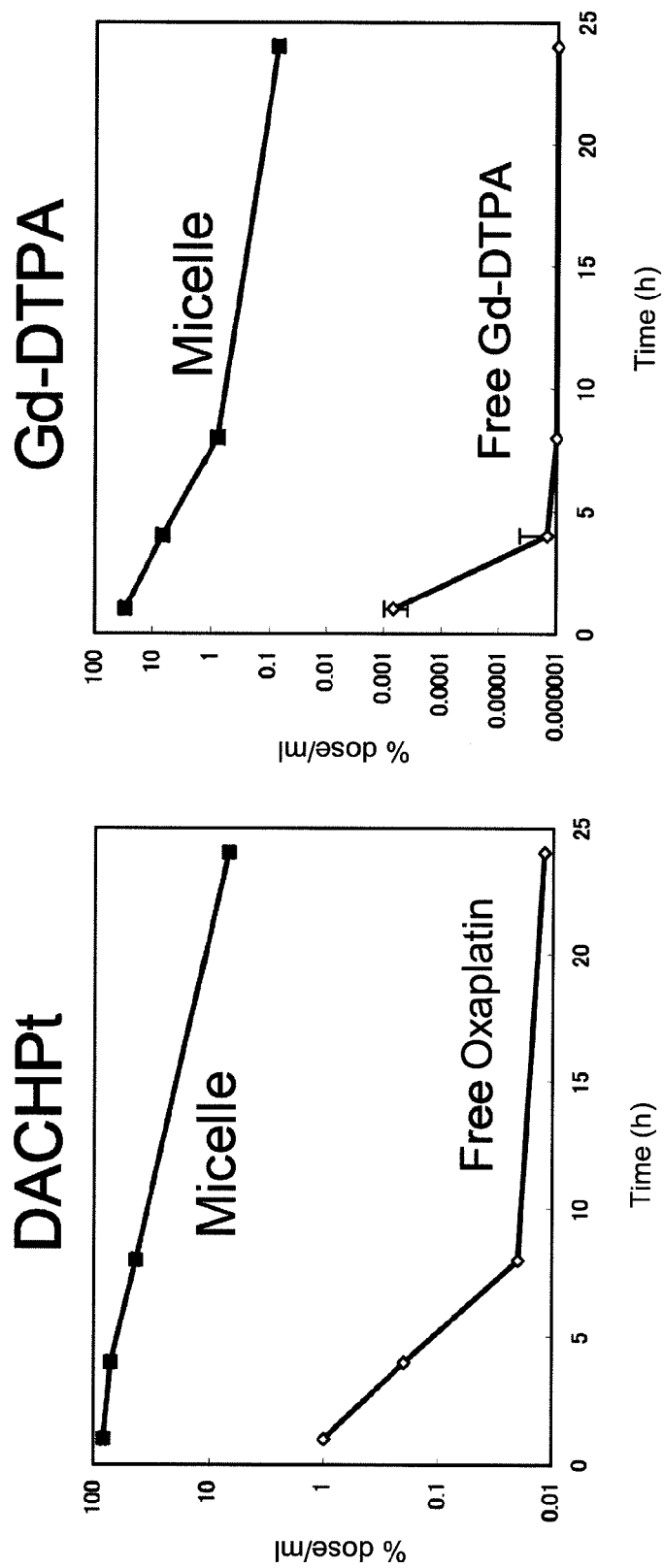

FIG. 12 is a graph showing the results measured for residual drug content (%) in plasma by collecting blood at 1, 4, 8 and 24 hours after injection of Gd-DTPA/DACHPt-encapsulating micelles and free oxaliplatin or free Gd-DTPA. In the case of the micelles, the drugs remained even after 24 hours, whereas oxaliplatin and Gd-DTPA were found to rapidly disappear from plasma. This result indicated that the micelles greatly increased the retention of both drugs in blood.

Figure 13:
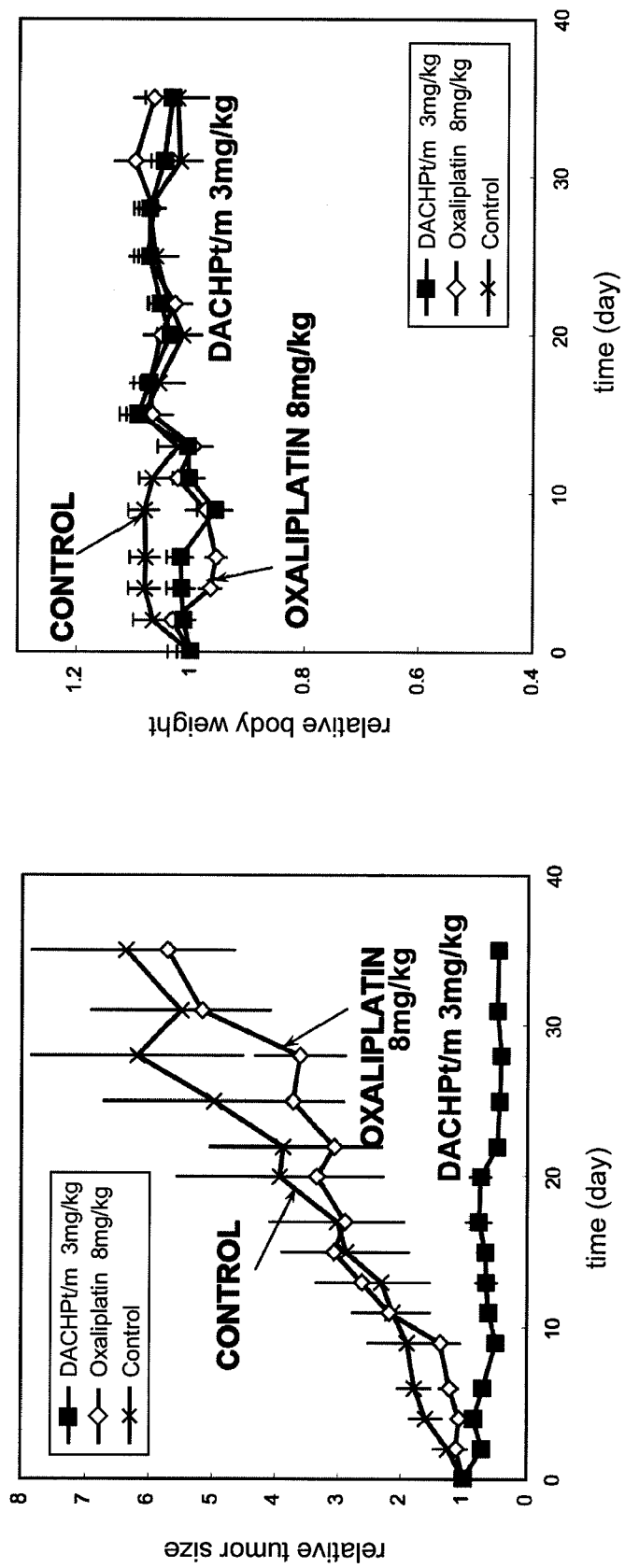

FIG. 13 presents graphs showing changes in tumor size (left panel) and body weight (right panel) in the non-treated group after administration of Gd-DTPA/DACHPt-encapsulating micelles (Pt concentration: 3 mg/ml) or oxaliplatin (Pt concentration: 8 mg/ml) against human pancreatic cancer (BxPC3), which is one of the intractable cancers. In these graphs, "DACHPt/m" represents the case where Gd-DTPA/DACHPt-encapsulating micelles were administered. Oxaliplatin showed little therapeutic effect even at a drug concentration twice or more higher than that of the micelles, whereas the micelles showed a sufficient anticancer effect even at a reduced dose. Moreover, there was no reduction in body weight, suggesting that the micelles had no strong side effect.

Figure 14:
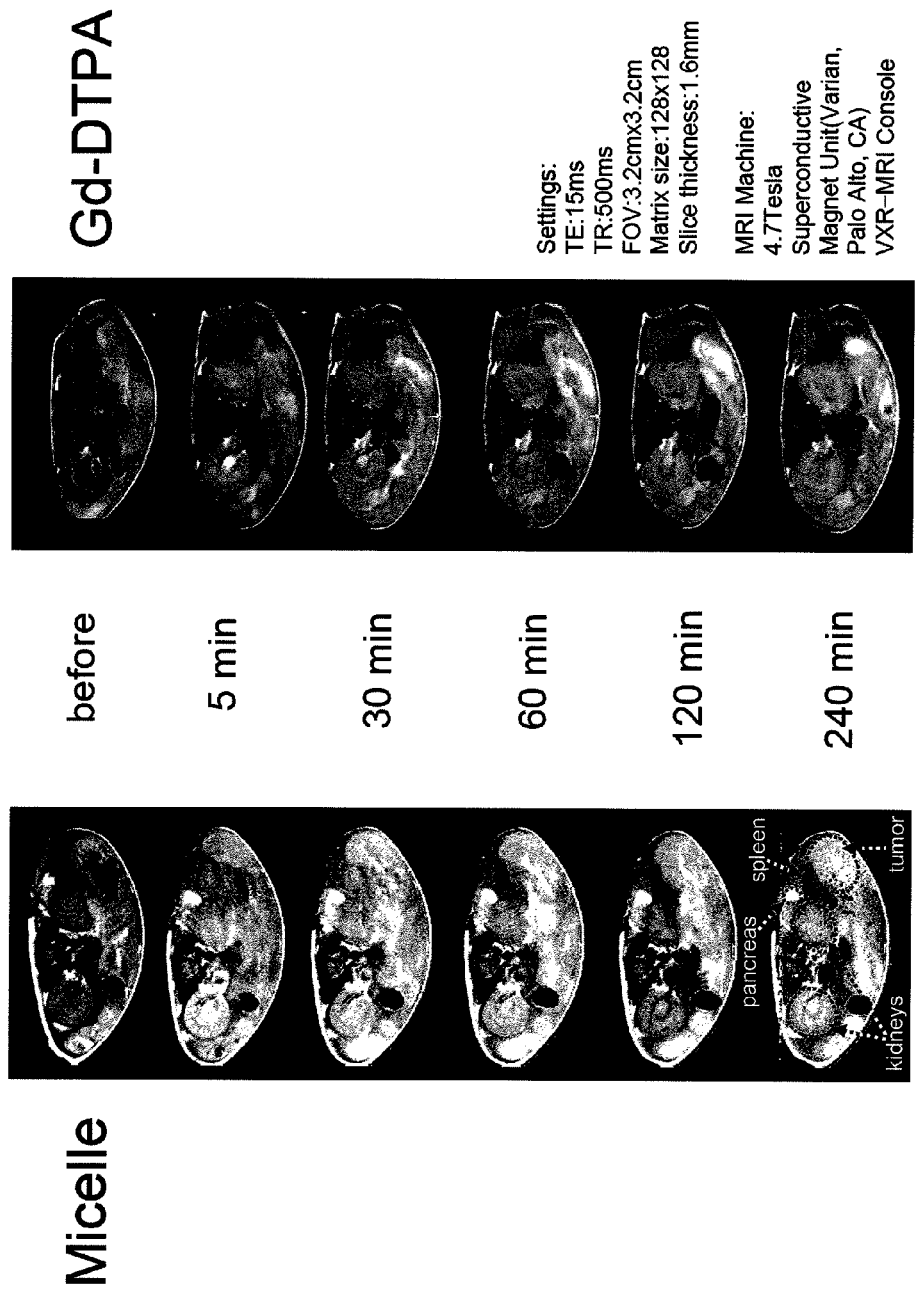

FIG. 14 presents MRI images showing the results of in vivo MRI experiment. In an orthotopic transplantation model of intractable human pancreas cancer (BxPC3), Gd-DTPA/DACHPt-encapsulating micelles (left) and Gd-DTPA (right) were confirmed for their MRI contrast effect after administration. The micelles were found to have a stronger and longer-lasting contrast enhancement than Gd-DTPA and hence established a clear difference in intensity between non-tumor organs and tumors, whereas Gd-DTPA had little contrast enhancement.

Figure 15:
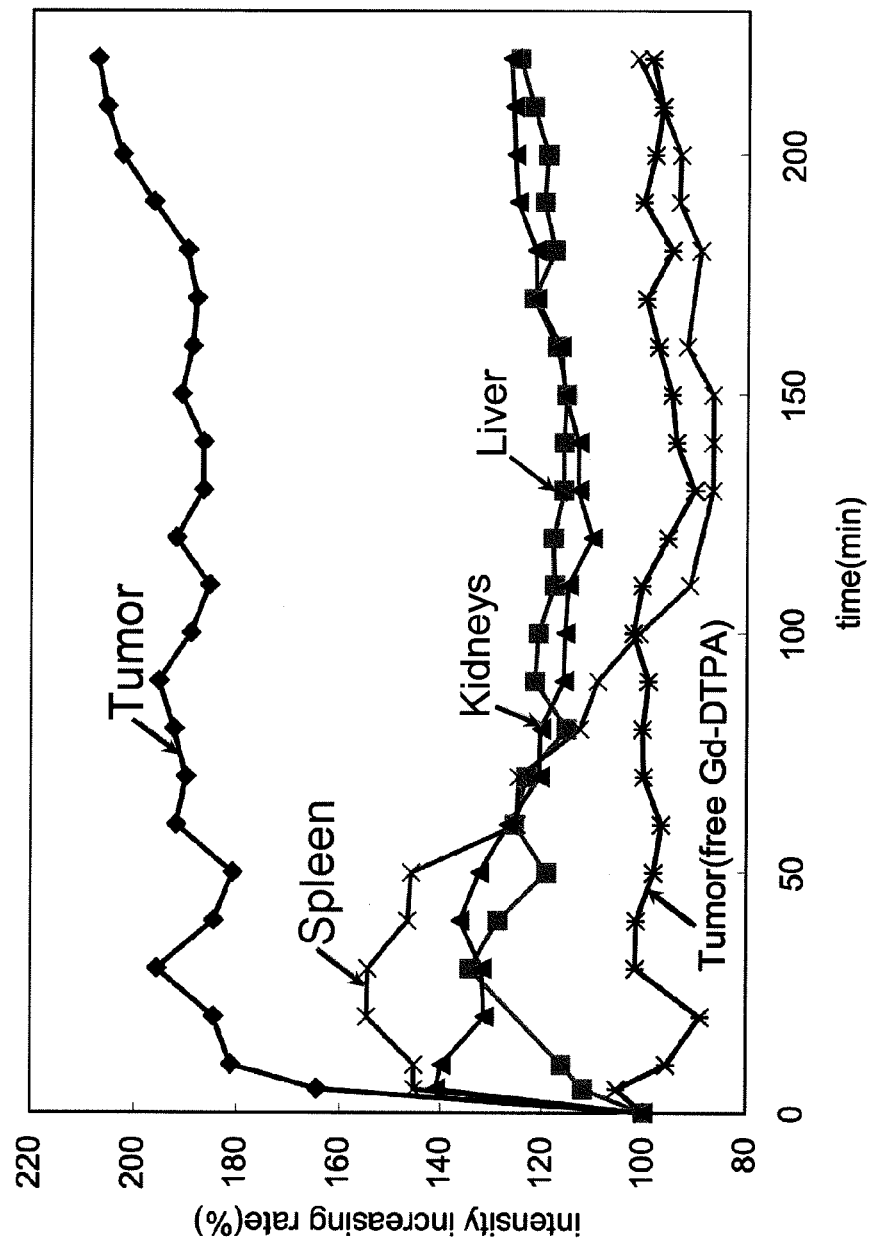

FIG. 15 is a graph showing time-dependent changes in mean intensity at each site in an in vivo MRI experiment. In tumors receiving Gd-DTPA (Tumor (free Gd-DTPA)), there was little increase in intensity, whereas tumors receiving Gd-DTPA/DACHPt-encapsulating micelles (Tumor) showed a significant and long-lasting increase in intensity. In other organs (Liver, Kidneys, Spleen), there was a slight increase in intensity, but this increase did not last because the drug was washed out.

BEST MODES FOR CARRYING OUT THE INVENTION

The present invention will be described in more detail below. The scope of the present invention is not limited by the description, and embodiments other than those specifically mentioned below can also be made with appropriate modifications, without departing from the spirit of the present invention.

It should be noted that this specification incorporates the entire specification of Japanese Patent Application No. 2008-167823 (filed on Jun. 26, 2008) based on which the present application claims priority. Moreover, all documents cited herein, including prior art documents, patent gazettes and other patent documents, are incorporated herein by reference.

1. Polymer-Metal Complex Composite

The present invention focuses on a drug delivery system based on polymeric micelles with high retention in blood and tumor tissue selectivity, and it aims to provide a block copolymer-metal complex composite used for encapsulation of a metal complex having MRI contrast ability within such polymeric micelles.

The polymer-metal complex composite of the present invention is a polymer-metal complex composite, which comprises a block copolymer (A) represented by the following general formula (a) and a metal complex (B) having MRI contrast ability:

poly(hph)-block-poly(carbo)    (a)

[wherein poly(hph) represents an uncharged hydrophilic polymer chain segment, and poly(carbo) represents a polymer chain segment having carboxyl groups in its side chain. It should be noted that the expression "poly(hph)" or "poly(carbo)" is used herein for convenience only and the term "poly" is intended to also encompass members falling within the scope of so-called "oligo"], wherein the composite comprises a structure in which a carboxyl anion of poly(carbo) in the copolymer (A) is attached to the metal complex (B) via a metal atom (M).

More specifically, the structure in which a carboxyl anion of poly(carbo) in the copolymer (A) is attached to the metal complex (B) via a metal atom (M) is preferably a structure in which the metal atom (M) is attached to the carboxyl anion of poly(carbo) in the copolymer (A), and the metal complex (B) is attached to the metal atom (M). The metal atom (M), which serves as a linker between the copolymer (A) and the metal complex (B), is not limited in any way and may be a metal atom alone or a metal atom in a compound containing the metal atom. A preferred example of the latter is a central metal atom in a metal complex. A preferred example of a central metal atom in a metal complex is, but not limited to, a central metal atom in a metal complex (C) having antitumor activity. In this case, it is possible to exert not only MRI contrast ability, but also antitumor activity. It should be noted that a preferred metal complex (C) is, but not limited to, one that is immobilized to the block copolymer (A) to ensure that the composite of the present invention has high stability in blood.

In the copolymer (A), preferred examples of poly(hph), which is an uncharged hydrophilic polymer chain segment, include but not limited to those derived from a hydrophilic polymer selected from the group consisting of polyethylene glycol (PEG), poly(2-methyl-2-oxazoline), poly(2-ethyl-2-oxazoline), poly(2-isopropyl-2-oxazoline), polyacrylamide, polymethacrylamide, polyvinyl alcohol, poly(hydroxyethyl acrylate) and poly(hydroxyethyl methacrylate). Among them, those derived from polyethylene glycol are more preferred.

Likewise, in the copolymer (A), preferred examples of poly(carbo), which is a polymer chain segment having carboxyl groups in its side chain, include but not limited to those derived from an anionic polymer selected from the group consisting of poly(glutamic acid), poly(aspartic acid), poly(acrylic acid), poly(methacrylic acid) and poly(malic acid). Among them, those derived from poly(glutamic acid) and poly(aspartic acid) are more preferred.

Specific examples of the polymer-metal complex composite of the present invention include composites represented by the following general formula (1) or (2).

[Chemical formula 31]

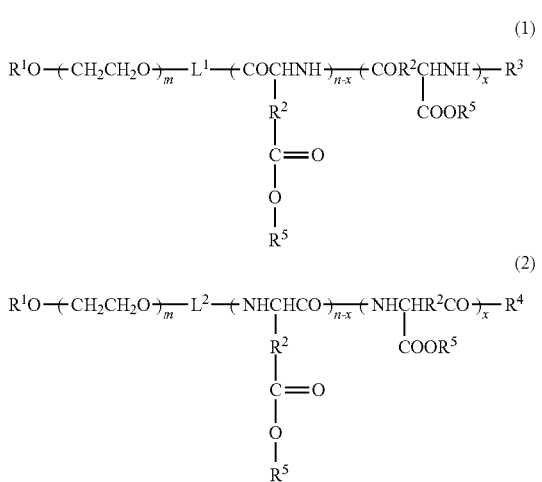

Moreover, other preferred specific examples of the polymer-metal complex composite of the present invention include composites represented by the following general formula (1-a) or (2-a).

[Chemical formula 32]

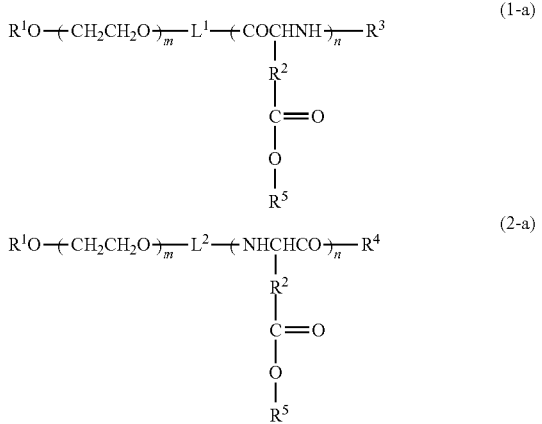

In the above formulae (1), (2), (1-a) and (2-a), $R^1$ represents a hydrogen atom or an unsubstituted or substituted linear or branched $C_{1-42}$ alkyl group, $L^1$ and $L^2$ each represent a linker group, $R^2$ independently represents a methylene group or an ethylene group, $R^3$ independently represents a hydrogen atom, a protecting group for an amino group, a hydrophobic group or a polymerizable group, $R^4$ represents a hydroxyl group or an initiator residue, and $R^5$ independently represents a hydrogen atom, an alkali metal ion, or a group represented by the following general formula (3) or (4):

[Chemical formula 33]

(wherein $R^6$ represents a metal atom or a group derived from a metal complex, and $R^7$ represents a group derived from a metal complex having MRI contrast ability). The group represented by general formula (4), which has two binding hands, is intended to mean a group that links two $R^5$ moieties (i.e., a group that is attached to two carboxyl anions). In addition, m represents an integer of 5 to 20,000 (preferably 10 to 5,000, more preferably 40 to 500), and n represents an integer of 2 to 5,000 (preferably 5 to 1,000, more preferably 10 to 200). Further, in the above formulae (1) and (2), x represents an integer of 0 to 5,000 (preferably 0 to 1,000, more preferably 0 to 200) (provided that x≤n). It should be noted that in the above formulae (1) and (2), n−x repeating units and x repeating units are not limited in any way and may be distributed at random or in a block pattern.

A moiety of m repeating units in the above formulae (1), (2), (1-a) and (2-a) corresponds to the poly(hph) segment in the above formula (a). Likewise, a moiety of n−x and x repeating units in the above formulae (1) and (2) or a moiety of n repeating units in the above formulae (1-a) and (2-a) corresponds to the poly(carbo) segment in the above formula (a).

With respect to $R^1$, examples of the above unsubstituted or substituted linear or branched $C_{1-12}$ alkyl group include, but are not limited to, methyl, ethyl, n-propyl, isopropyl, n-butyl, sec-butyl, tert-butyl, n-pentyl, n-hexyl, decyl, undecyl and so on. In the case of substituted alkyls, examples of substituents include an acetal-protected formyl group, a cyano group, a formyl group, a carboxyl group, an amino group, a $C_{1-6}$ alkoxycarbonyl group, a $C_{2-7}$ acylamido group, a tri-$C_{1-6}$ alkylsiloxy group whose alkyls are the same or different, a siloxy group or a silylamino group. When a substituent is an acetal-protected formyl group, it may be hydrolyzed under acidic mild conditions and converted into another substituent, i.e., a formyl group (—CHO or an aldehyde group). Such a formyl group or the above carboxyl or amino group can be obtained, for example, by deprotection or conversion from a corresponding protected group or moiety after the composite of the present invention is generated. Then, it may optionally be used for covalent bonding with an appropriate antibody or a fragment thereof having specific binding properties (e.g., F(ab')$_2$, F(ab), or folic acid) to thereby provide the composite with targeting properties. A poly(hph) segment having such a functional group at its one end (i.e., an uncharged hydrophilic polymer chain segment) can be formed, for example, according to the method described in WO 96/32434, WO 96/33233 or WO 97/06202 for the preparation of PEG segments in block copolymers. The poly(hph) segments thus formed and poly(carbo) segments may be linked in any mode and may be linked via any linker group, according to the above-mentioned method for the preparation of each block copolymer. Such a preparation method is as follows, but is not limited to: a poly(hph) derivative having an amino group at its end is used and polymerized at its amino end, for example, with N-carboxylic acid anhydride (NCA) of β-benzyl-L-aspartate and/or γ-benzyl-L-glutamate to synthesize a block copolymer, followed by conversion of side chain benzyl groups into other ester groups or by partial or complete hydrolysis to thereby obtain a desired block copolymer. In this case, the resulting copolymer has a copolymer structure constituting a composite of general formula (1) or (1-a), and the linker group $L^1$ has a structure derived from the terminal structure of the poly(hph) segment used, preferably —$(CH_2)_p$—NH— (wherein p is an integer of 1 to 5). Alternatively, it is also possible to prepare a copolymer by another method in which a poly(carbo) segment or a poly(carbo) derivative is synthesized and then linked to a poly(hph) segment which has been prepared. In this case, some of the resulting copolymers may eventually have the same structure as those prepared by the above method, and others may have a copolymer structure constituting a composite of general formula (2) or (2-a). The linker group $L^2$ is not limited in any way and is preferably —$(CH_2)_q$—CO— (wherein q is an integer of 1 to 5).

With respect to $R^3$, examples of the above protecting group for an amino group include a benzyloxycarbonyl group, a t-butyloxycarbonyl group, an acetyl group and a trifluoroacetyl group, etc. Likewise, examples of the hydrophobic group include a benzylcarbonyl group and a benzhydrylcarbonyl group, etc. Further, examples of the polymerizable group include acryloyl and methacryloyl groups, etc.

With respect to $R^4$, examples of the above initiator residue include an aliphatic or aromatic primary amine compound residue (—NH-alkyl) and the like, which can serve as an initiator of NCA polymerization.

With respect to $R^5$, examples of the above alkali metal ion include sodium (Na) ion, lithium (Li) ion and potassium (K) ion, etc.

Moreover, examples of $R^6$ in the groups represented by general formulae (3) and (4) include metal atoms such as platinum (Pt), copper (Cu), gold (Au) and iron (Fe), as well as a group derived from a metal complex having platinum, copper, gold or iron as a central metal atom. In this case, examples of the group derived from a metal complex include, but are not limited to, groups represented by the following general formulae (5) and (6). It should be noted that the group represented by general formula (6) may have either a cis or trans structure.

[Chemical formula 34]

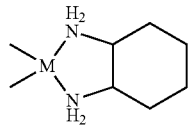

(5)

(6)

[wherein M represents a metal atom selected from platinum, copper, gold or iron]

Alternatively, a preferred example of the group derived from a metal complex, which serves as $R^6$, is a group derived from a metal complex having antitumor activity, as specifically exemplified by groups represented by the following formulae (5-a) and (6-a). In this case, the group represented by formula (5-a) is a group derived from diaminocyclohexane platinum(II) complex (DACH Platin (DACHPt)), while the group represented by formula (6-a) is a group derived from cisplatin (CDDP). It should be noted that although the group represented by formula (6-a) may also include a transplatin-derived group, a cisplatin-derived group is selected as a group derived from a metal complex having antitumor activity.

[Chemical formula 35]

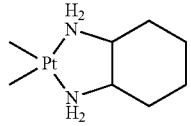

(5-a)

(6-a)

Next, $R^7$ in the group represented by general formula (3) is not limited in any way as long as it is a group derived from a metal complex having MRI contrast ability, and preferred examples include groups derived from a metal complex having gadolinium, europium, manganese, iron or copper as a central metal atom. Such a metal complex is preferably a metal complex with a multidentate ligand, and in a more preferred embodiment, such a multidentate ligand is an aminocarboxylic acid or phosphoric acid compound, a porphyrin compound, or deferrioxamine B. Moreover, preferred examples of an aminocarboxylic acid or phosphoric acid compound serving as a multidentate ligand include ethylene diamine tetraacetic acid, diethylene triamine pentaacetic acid, diethylene triamine pentaacetic acid bismethylamide, triethylene tetramine hexaacetic acid, benzyloxypropionic pentaacetic acid, ethylene glycol tetramine tetraacetic acid, tetraazacyclododecane tetraacetic acid, tetraazacyclododecane triacetic acid, dihydroxyhydroxymethylpropyltetraazacyclododecane triacetic acid, hydroxypropyltetraazacyclododecane triacetic acid, and tetraazacyclododecane tetraphosphoric acid, etc. Among them, more preferred are ethylene diamine tetraacetic acid, diethylene triamine pentaacetic acid, diethylene triamine pentaacetic acid bismethylamide, tetraazacyclododecane tetraacetic acid, and hydroxypropyltetraazacyclododecane triacetic acid.

Specific examples of the above group derived from a metal complex, which serves as $R^7$, include groups represented by the following general formulae (7), (8), (9) and (10).

[Chemical formula 36]

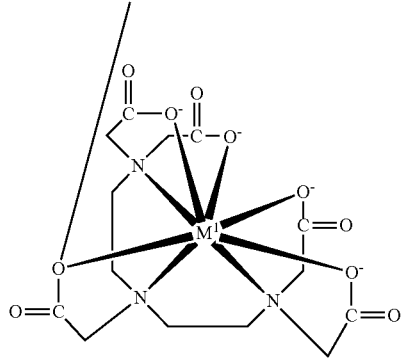

(7)

[Chemical formula 37]

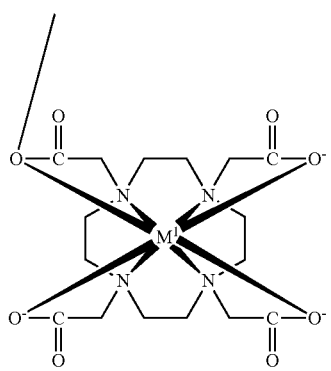

(8)

[Chemical formula 38]

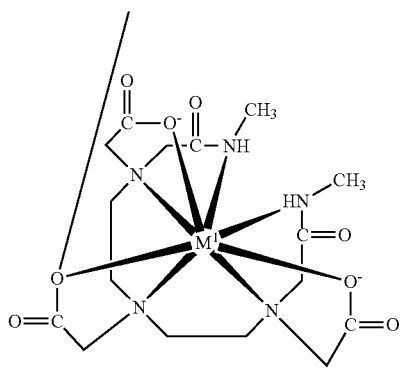

(9)

[Chemical formula 39]

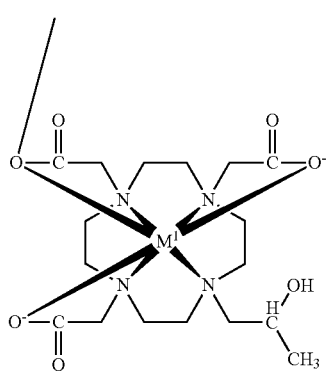

(10)

[wherein $M^1$ represents a metal atom selected from gadolinium, europium, manganese, iron or copper]

More specific examples of the above group derived from a metal complex, which serves as $R^7$, include groups represented by the following formulae (7-a), (8-a), (9-a) and (10-a).

[Chemical formula 40]

(7-a)

[Chemical formula 41]

(8-a)

[Chemical formula 42]

(9-a)

[Chemical formula 43]

(10-a)

Further, examples of the group represented by general formula (3), which serves as $R^5$, include groups composed of $R^6$ and $R^7$ shown above, as specifically exemplified by groups represented by the following general formulae (11), (12), (13), (14), (15), (16), (17) and (18), more specifically groups represented by the following formulae (11-a), (12-a), (13-a), (14-a), (15-a), (16-a), (17-a) and (18-a).

[Chemical formula 44]

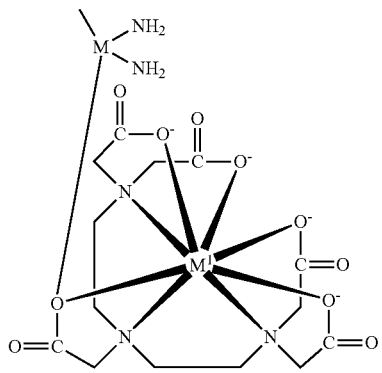

(11)

[Chemical formula 45]

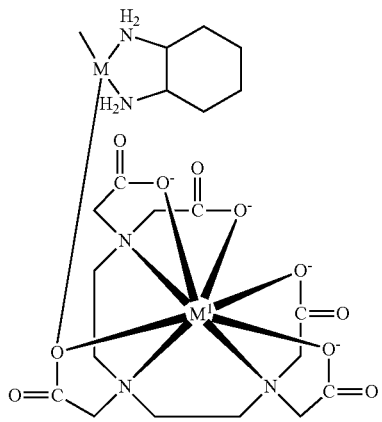

(12)

[Chemical formula 46]

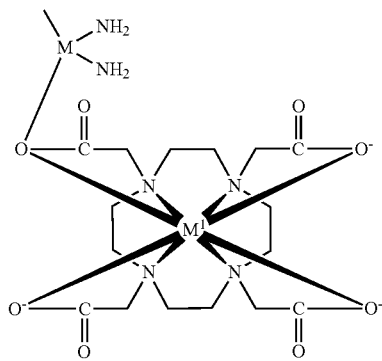

(13)

[Chemical formula 47]

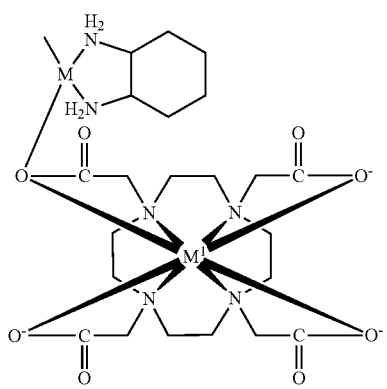

(14)

[Chemical formula 48]

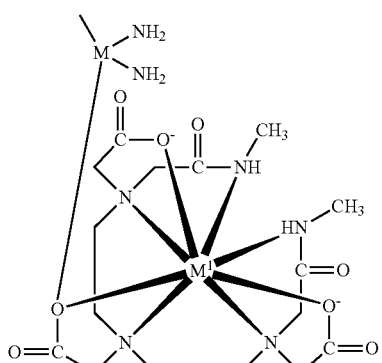

(15)

[Chemical formula 49]

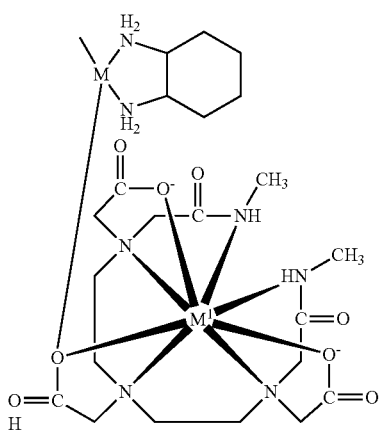

(16)

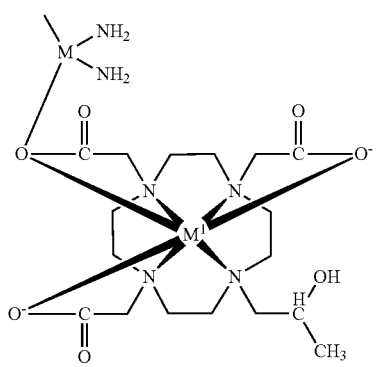

(17)

-continued
[Chemical formula 51]
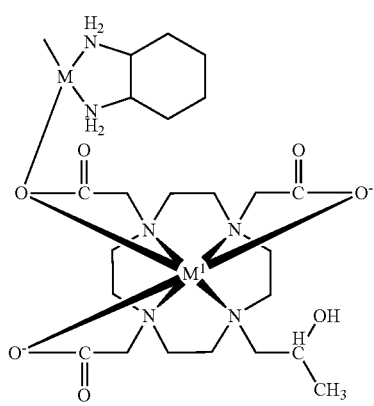
(18)
[wherein M¹ represents a metal atom selected from platinum, copper, gold or iron, or M¹ represents a metal atom selected from gadolinium, europium, manganese, iron or copper]
[Chemical formula 52]
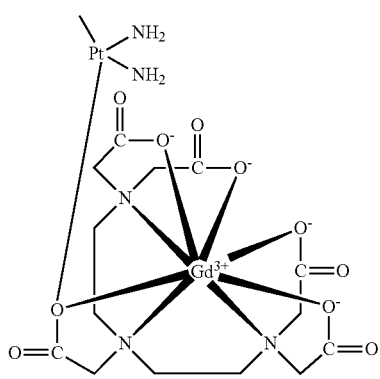
(11-a)
[Chemical formula 53]
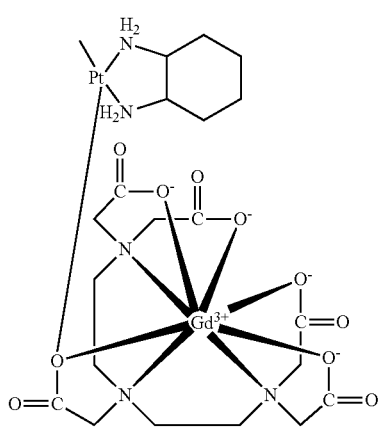
(12-a)
-continued
[Chemical formula 54]
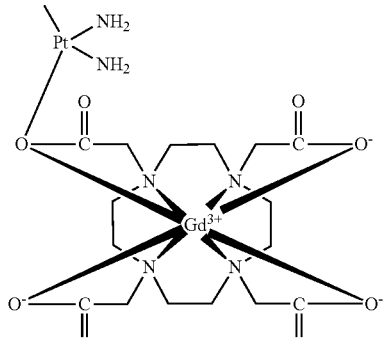
(13-a)
[Chemical formula 55]
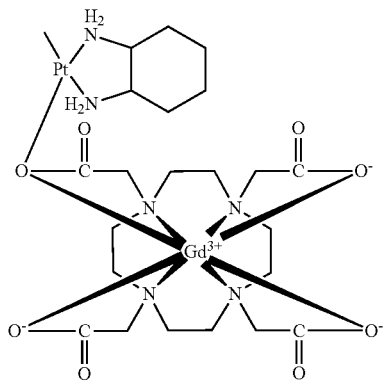
(14-a)
[Chemical formula 56]
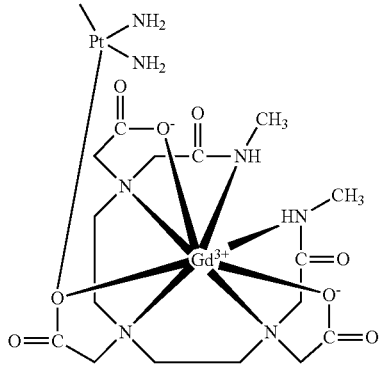
(15-a)
[Chemical formula 57]
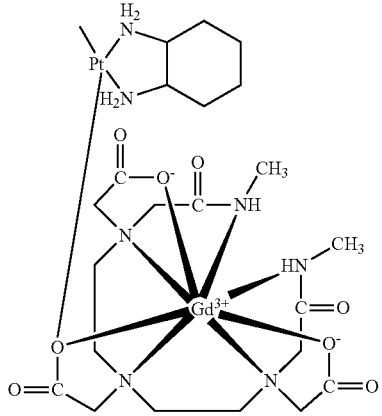
(16-a)

[Chemical formula 58]

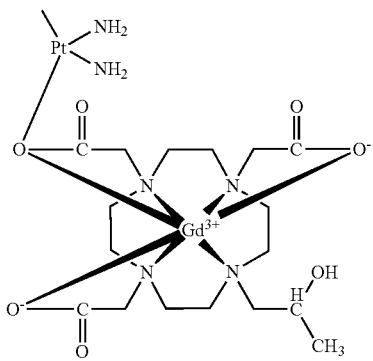

(17-a)

[Chemical formula 59]

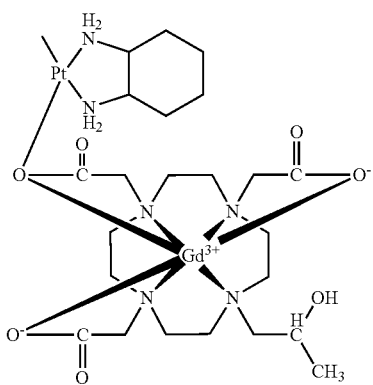

(18-a)

In the composite of the present invention represented by the above general formula (1), (2), (1-a) or (2-a), $R^5$ comprises, at least in part, the group represented by general formula (3) described above. The percentage of the group represented by general formula (3) is not limited in any way, and for example, it is preferably 0.01% or more, more preferably 0.1% or more, and even more preferably 1% or more, relative to $R^5$ (n units in total) contained in the composite of the present invention represented by the above formula (1), (2), (1-a) or (2-a).

Any method may be used to prepare the polymer-metal complex composite of the present invention. In a preferred embodiment, the block copolymer (A) and the metal complex (B) having MRI contrast ability described above are reacted in the presence of a metal atom (M) (including a metal complex such as a metal complex (C) having antitumor activity) in an aqueous medium. The reaction conditions may be set to any conditions as long as a desired polymer-metal complex composite can be obtained. For example, the amounts of copolymer (A), metal complex (B) and metal atom (M) to be used can be set as appropriate to give the above composite structure represented by general formula (1), (2), (1-a) or (2-a). It should be noted that when the above metal complex (C) is used as a metal atom (M), for example, the amounts to be used are preferably determined such that the equivalent ratio of DACH Platin or cisplatin relative to carboxyl groups in the copolymer (A) (i.e., metal complex (C)/carboxyl groups in copolymer (A)) is 1/10000 or more, preferably 1/1000 or more, and more preferably 1/100 or more. Moreover, the reaction temperature is not limited in any way and is preferably, for example, 5° C. to 60° C. Furthermore, the aqueous medium serving as a reaction solvent may comprise water (particularly deionized water) or various inorganic or organic buffers, or water-miscible organic solvents such as acetonitrile, dimethylformamide, ethanol and so on within a range that does not affect the formation reaction of the composite of the present invention.

With respect to the form of the composite of the present invention, for example, preferred are those encapsulating the metal complex having MRI contrast ability within micellar particles whose shell and core are formed by the poly(hph) and poly(carbo) segments, respectively, and more preferred are those further encapsulating a metal complex having antitumor activity. In general, in an aqueous medium (aqueous solvent), the composite of the present invention can aggregate to form a solubilized polymeric micellar state. The poly(hph) segment, which is a hydrophilic polymer chain segment, constitutes the shell of micellar particles on the surface side, while the poly(carbo) segment, which is a hydrophobic polymer chain segment, constitutes the core inside the micellar particles. The metal complex having MRI contrast ability or the metal complex having antitumor activity, which is attached to the poly(carbo) segment, is encapsulated within micellar particles together with the poly(carbo) segment constituting the core. Such polymeric micellar particles constituted from the composite of the present invention preferably have an average dispersed particle size of, for example, 10 nm to 1 μm, more preferably 10 nm to 200 nm, and even more preferably 20 nm to 50 nm in an aqueous medium, as measured by dynamic light scattering. The polymeric micellar particles can be isolated and purified in a routine manner from the aqueous medium. Typical techniques used for this purpose include ultrafiltration, diafiltration, and dialysis.

2. MRI Contrasting and/or Antitumor Composition

The present invention provides an MRI contrasting composition and/or an antitumor composition (pharmaceutical composition), which comprises the polymer-metal complex composite described above. The composition of the present invention can be used as an MRI-based detection/diagnosis means for cancer (malignant tumor) and/or as a therapeutic means for cancer (malignant tumor). The type of tumor is not limited in any way, and various known types of cancers are intended.

In the composition of the present invention, the content of the above polymer-metal complex composite is not limited in any way and may be set as appropriate in consideration of MRI contrast effect and/or antitumor effect.

The composition of the present invention may be applied to various types of animals including, but not limited to, humans, mice, rats, rabbits, pigs, dogs, cats and so on. For administration to an animal subject, parenteral routes such as intravenous drip infusion are generally used, and individual conditions including dosage, administration frequency and administration period may be set as appropriate depending on the type and condition of the animal subject, as well as the intended use of the composition. For example, in the case of intravenous administration in humans to obtain an antitumor effect, the dose is preferably determined by a medical specialist in consideration of the results of small-scale experiments with laboratory animals or volunteers and in further consideration of the patient's condition. Without being limited thereto, the dose may usually be set to 1.0 to 1,000 mg/m² (patient's body surface area), given once a day. An appropriate dose may be selected depending on the administration schedule used, for example, 10 to 200 mg/m² (patient's body surface area) is administered once a day for several consecutive days, followed by withdrawal for a given period, or alternatively, 50 to 500 mg/m² (patient's body surface area) is administered once a day, followed by withdrawal for several days.

In consideration of the intended use (i.e., MRI contrasting and/or antitumor purposes), the composition of the present invention may be used in combination with appropriate materials generally used in drug production, selected from excipients, fillers, extenders, binders, wetting agents, disintegrants, lubricants, surfactants, dispersants, buffers, preservatives, solubilizers, antiseptics, correctives, soothing agents, stabilizers and isotonizing agents, etc.

The present invention enables the provision of an MRI contrasting method for tumor detection, which comprises administering the polymer-metal complex composite of the present invention or the composition of the present invention described above to the body of an animal subject. Similarly, the present invention also enables the provision of a method for cancer treatment, which comprises administering the polymer-metal complex composite of the present invention or the composition of the present invention described above to the body of an animal subject.

3. MRI Contrasting and/or Antitumor Kit

The MRI contrasting and/or antitumor kit of the present invention comprises the polymer-metal complex composite described above. This kit can be preferably used in an MRI contrasting method for tumor detection or in a method for cancer treatment, etc.

In this kit, the polymer-metal complex composite of the present invention (including the composite in the form of polymeric micellar particles) may be stored in any state, and a solution or powder state may be selected in consideration of its stability (storage stability) and usability.

The kit of the present invention may further comprise other components in addition to the above polymer-metal complex composite. Examples of other components include, but are not limited to, various buffers, antiseptics, dispersants, stabilizers, and instructions for use (instruction manual for use), etc.

The present invention will be further described in more detail by way of the following illustrative examples, which are not intended to limit the scope of the invention.

Example 1

Figure 1:
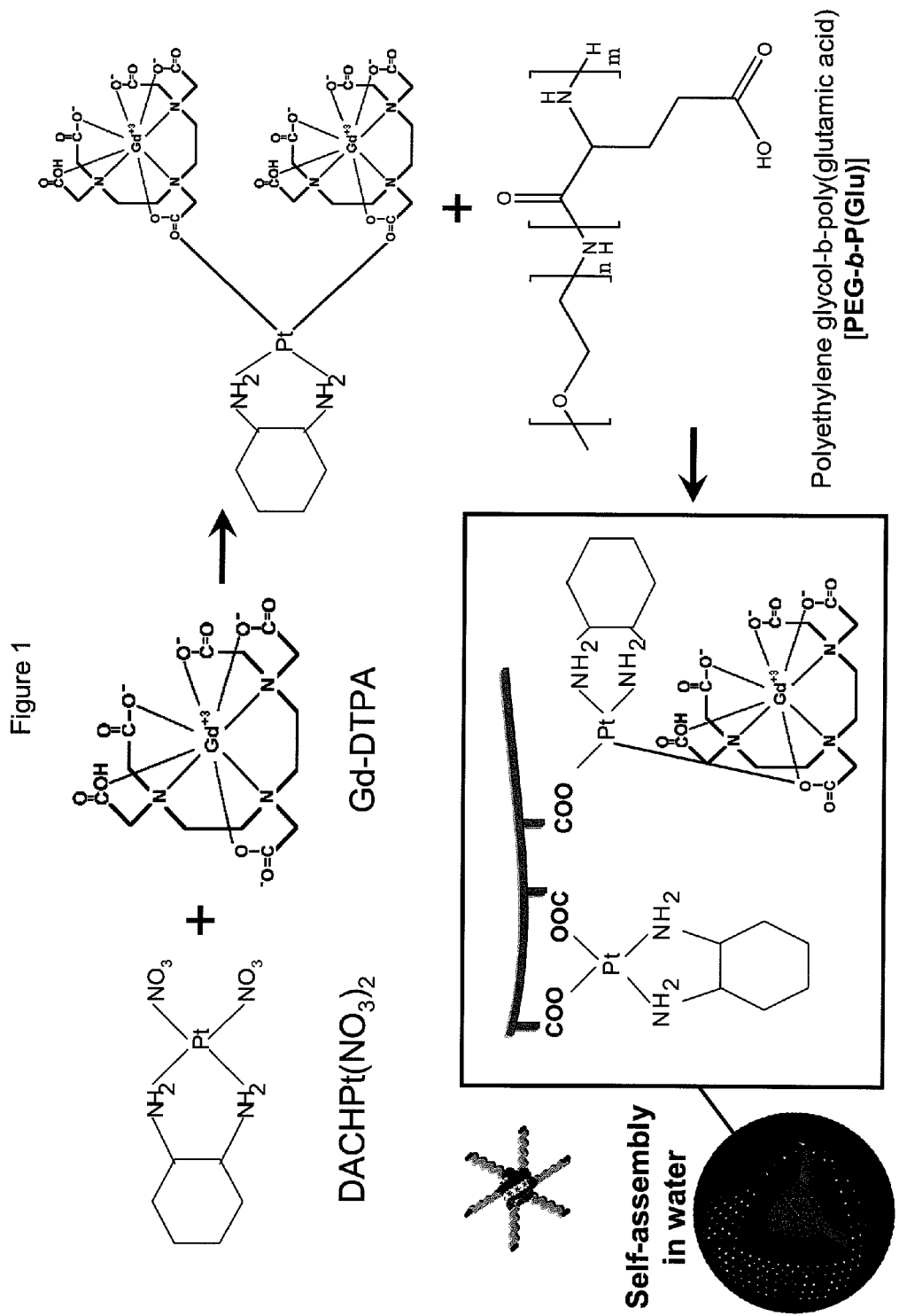
FIG. 1 is a schematic diagram showing a synthesis scheme for one embodiment of the polymer-metal complex composite of the present invention.

A metal complex was attached to a polyethylene glycol (hereinafter referred to as PEG)-polyamino acid copolymer, and a Gd (gadolinium) complex was further attached to the carboxyl terminal of the metal complex. The resulting polymer-metal complex composite was used to prepare micelles (FIG. 1).

More specifically, a 1-5 mM solution of cis-diamminedichloroplatinum(II) $Cl_2$ (hereinafter referred to as CDDP) or dichloro(1,2-diaminocyclohexane)platinum(II) $(NO_3)_2$ (hereinafter referred to as DACHPt) was used as a Pt complex, and 1-5 mM DACHPt$(NO_3)_2$ or 1-5 mM CDDP$Cl_2$ was first dissolved in distilled water at 70° C., followed by addition of 1-20 mM gadolinium diethylene triamine pentaacetic acid (hereinafter referred to as Gd-DTPA) or 5 mM gadolinium [5,8-bis(carboxymethyl)-11-[2-(methylamino)-2-oxoethyl]-3-oxo-2,5,8,11-tetraazamidecan-13-oato(3-)] (hereinafter referred to as gadodiamide). The mixture was shaken in the dark at 37° C. for 24 hours to prepare a Gd-DTPA/DACHPt, CDDP/Gd-DTPA, DACHPt/gadodiamide or CDDP/gadodiamide composite. Next, a PEG-polyglutamic acid copolymer or a PEG-polyaspartic acid copolymer was added at a carboxylic acid concentration of 2.5 to 5 mM and shaken in the dark at 37° C. for 5 days. Then, to remove the remaining excess Gd complex, Pt complex and polymer, a dialysis membrane with a molecular weight cut off (hereinafter referred to as MWCO) of 2,000 was used for dialysis for 24 hours, followed by ultrafiltration (3,000 rpm, 15 min, 5 times) using a filtration system with a MWCO of 30,000. Large-sized aggregates were removed with a 0.22 µm filter to obtain desired polymeric micelles.

Figure 2:
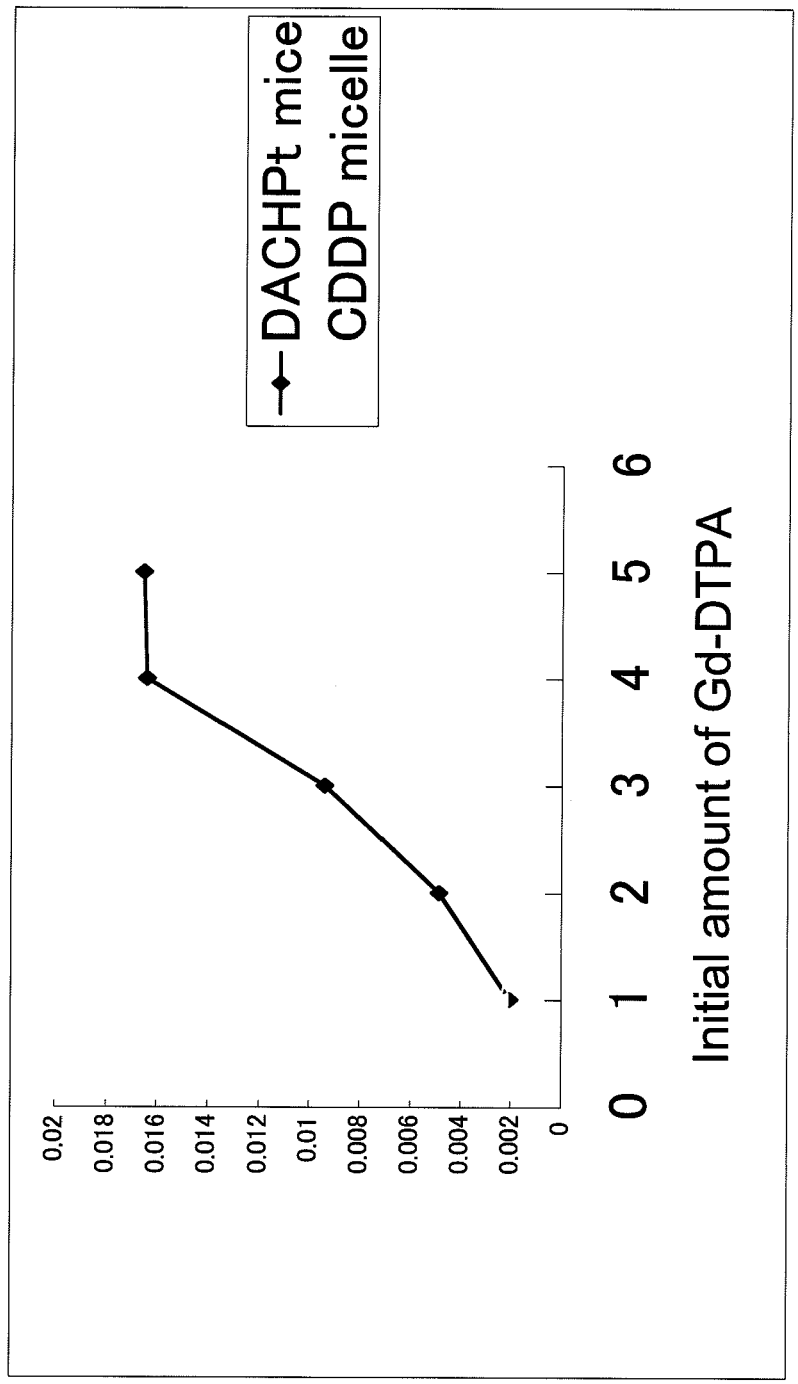
FIG. 2 is a graph showing the ratio of Gd encapsulated within micelles per polymer. This figure shows the amount of Gd finally encapsulated within micelles per polymer, relative to the amount of Gd-DTPA (mM) added during synthesis. The group using CDDP (yellow) showed consistently low Gd content, whereas the group using DACHPt (blue) showed a higher Gd content at a larger amount of Gd added during synthesis.

The amount of Gd complex encapsulated within the micelles was evaluated. More specifically, a 5 mM DACHPt solution or a 5 mM CDDP solution was first used to prepare micelles by varying the concentration of Gd-DTPA to be added, thereby investigating a concentration at which Gd was most efficiently contained. The block copolymer used was PEG-polyglutamic acid (molecular weight of PEG: 12,000, glutamic acid unit: 20). The amounts of Gd and Pt encapsulated within the micelles were determined as follows: the micelles were dissolved in 2% nitric acid, diluted 10000- to 100000-fold, and then analyzed by ion coupling plasma mass spectrometry (hereinafter referred to as ICP-MS) (Hewlett Packard 4500). As a result, the Gd content per polymer was higher in DACHPt-encapsulating micelles than in CDDP-encapsulating micelles, and the amount of Gd encapsulated within the micelles was higher when Gd-DTPA was added at a higher concentration (FIG. 2).

The amount of Gd-DTPA was varied from 1 to 20 mM, indicating that there was no increase in the amount of Gd-DTPA encapsulated within the micelles even when the Gd-DTPA concentration was elevated to 5 mM or higher.

Figure 3:
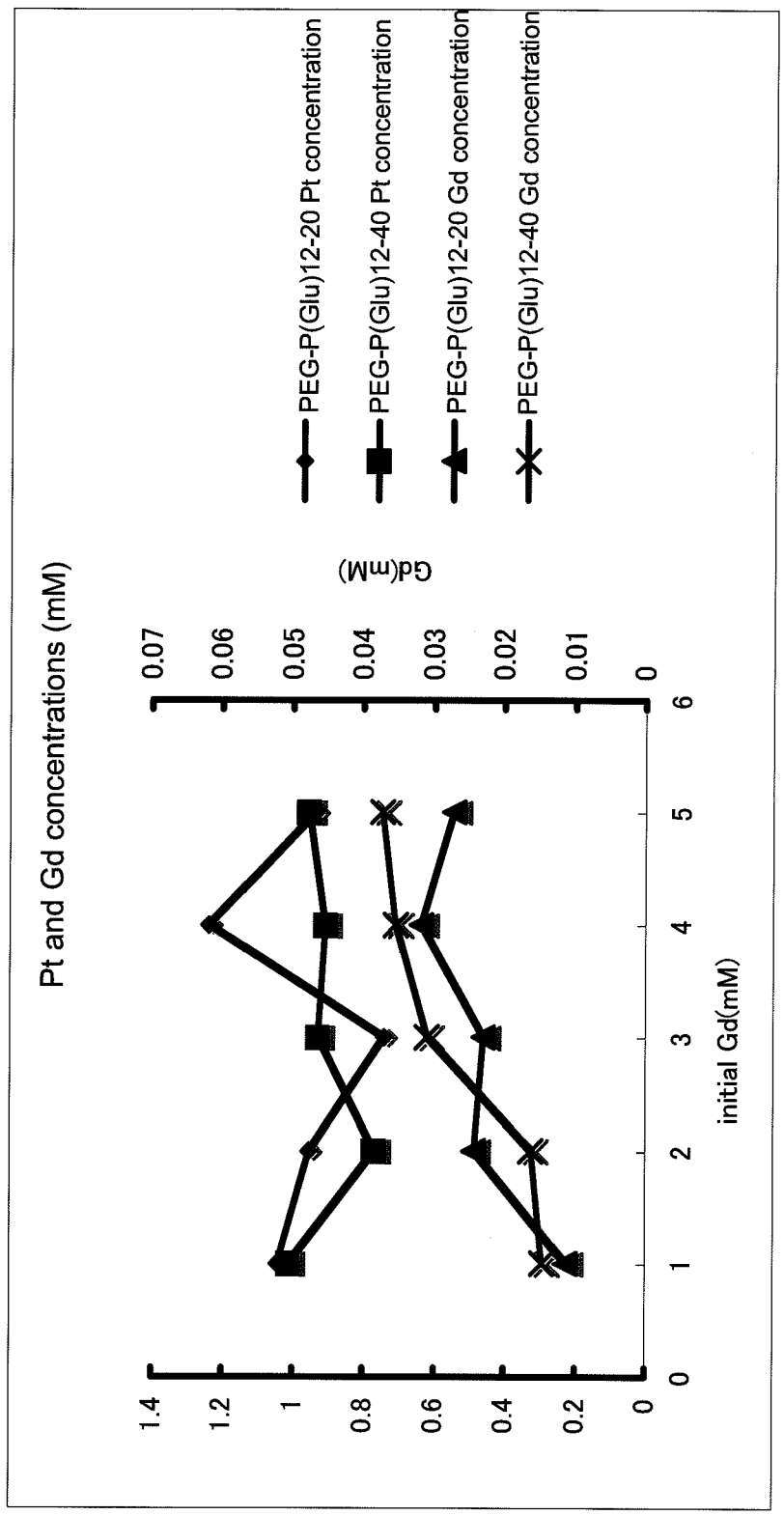
FIG. 3 is a graph showing the concentrations of Gd and Pt encapsulated within micelles. This figure shows Pt and Gd concentrations in PEG-P(Glu)12-20 and PEG-P(Glu)12-40. The Gd concentration was slightly higher in PEG-P(Glu)12-40 although there was no statistical significance.
Figure 4:
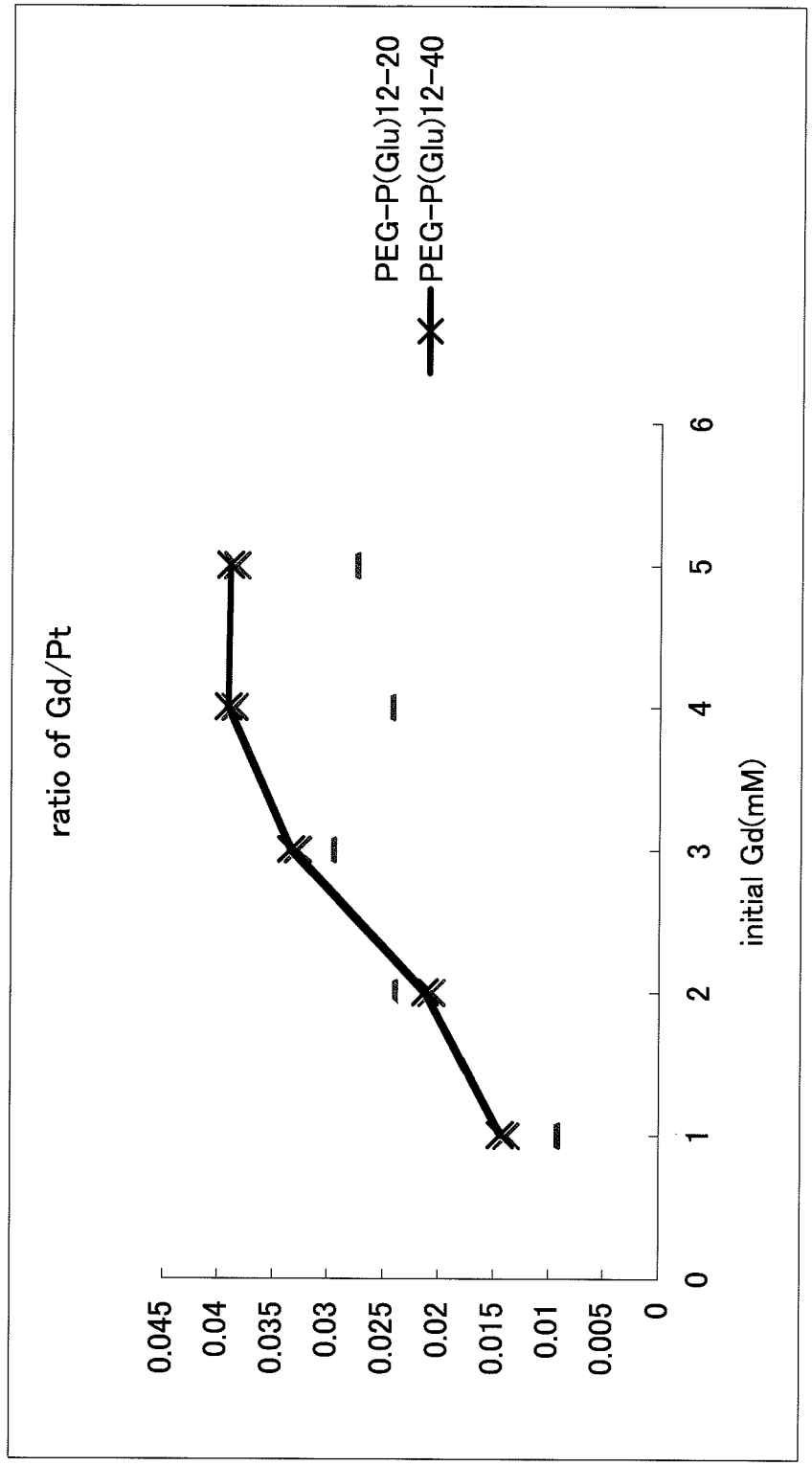
FIG. 4 is a graph showing the ratio of Gd to Pt encapsulated within micelles. This figure shows the Gd/Pt ratio for each of PEG-P(Glu)12-20 and PEG-P(Glu)12-40 micelles. When the amount of Gd initially added was 4 mM and 5 mM, the Gd/Pt ratio was slightly higher in PEG-P(Glu)12-40.

Another study was conducted to investigate whether the amount of Gd encapsulated within micelles would vary depending on the number of glutamic acid units in PEG-polyglutamic acid copolymer (PEG-PGlu). The block copolymer used was composed of PEG with a molecular weight of 12,000 and 20 or 40 units of polyglutamic acid (hereinafter referred to as PEG-PGlu(12-40) or PEG-PGlu(12-20), respectively, wherein the expression "12" means the molecular weight of PEG (i.e., 12,000) and the expression "20" or "40" means the number of polycarboxylic acid units (i.e., polyglutamic acid units in this case)). To prepare micelles, a 1-5 mM Gd-DTPA solution and a 5 mM DACHPt solution were first mixed and shaken in the dark at 37° C. for 24 hours, and then mixed with a 5 mM PEG-PGlu solution (calculated as carboxylic acid) and shaken at 37° C. for 5 days. In the same manner as described above, dialysis, ultrafiltration and a 0.22 µm filter were used to remove excess molecules and constructs, thereby obtaining desired polymeric micelles. Then, the amounts of Gd and Pt encapsulated within the micelles were determined as follows: the micelles were dissolved in 2% nitric acid, diluted 10000- to 100000-fold, and then analyzed by ICP-MS. As a result, the Gd/Pt ratio was slightly higher in PEG-PGlu(12-40) than in PEG-PGlu(12-20) although there was no statistical significance (FIGS. 3 and 4).

Figure 5:
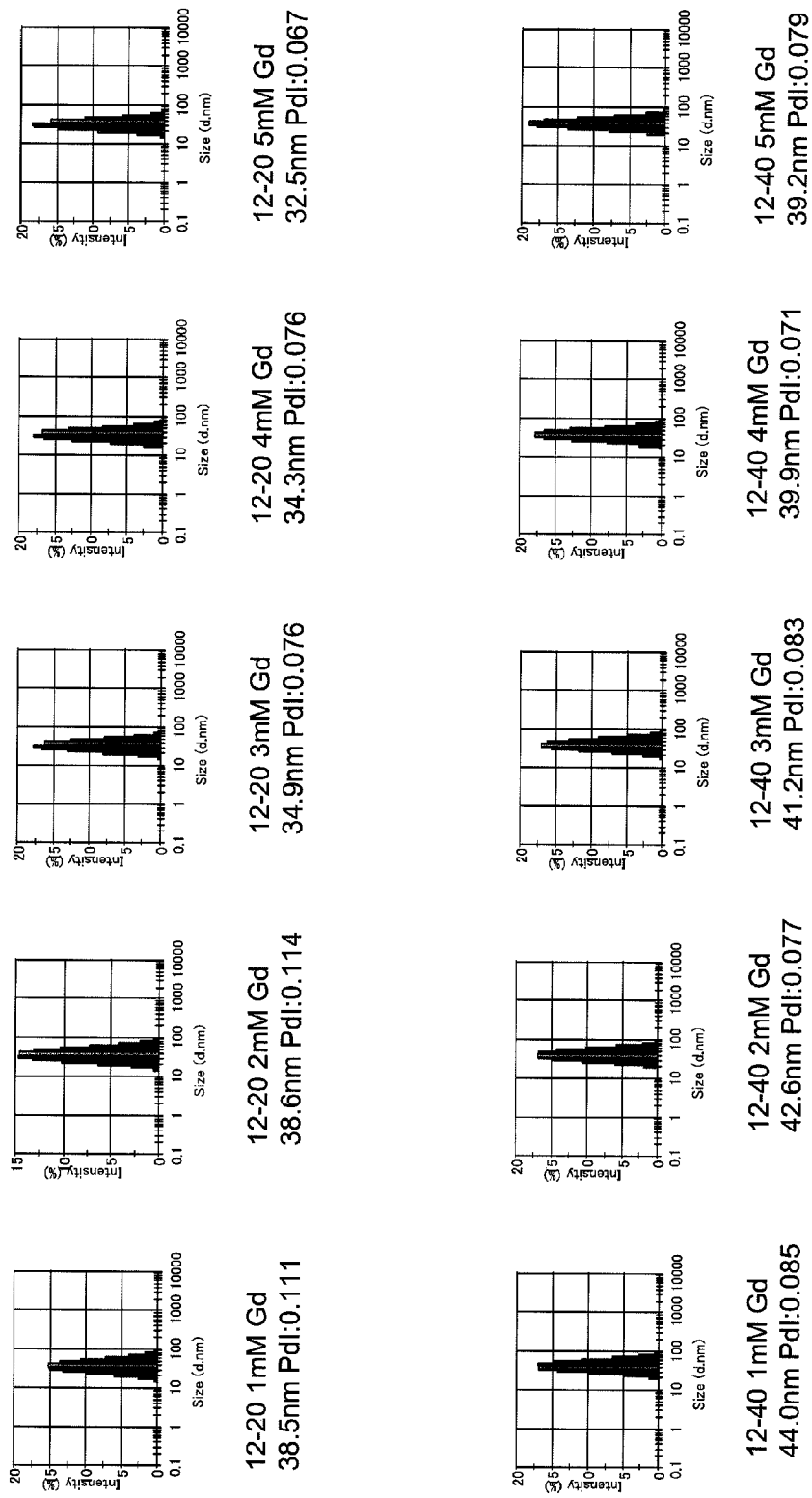
FIG. 5 presents charts showing the size of micelles (DLS data). Monodisperse particles with a particle size of 34 to 43 nm were obtained for all samples, and the Polydispersity Index (PdI) was found to be 0.1 or less in each case.

Yet another study was conducted to investigate whether the particle size of micelles would vary depending on the number of glutamic acid units in PEG-PGlu and the initial concentration of Gd-DTPA. The prepared micelles were measured for their hydrodynamic radius by dynamic light scattering (DLS) (Zetasizer Nano ZS, Malvern Instruments). As a result, the average particle size was 34 to 40 nm in the micelles prepared with each polymer, and the Polydispersity Index (PdI) was found to be 0.2 or less in each case, indicating that the micelles were monodisperse (FIG. 5).

As another example, the polymeric micelles shown below were also prepared and measured for their average particle size and PdI in the same manner as shown above. Namely, 5 mM gadodiamide and 5 mM DACHPt were reacted, followed by addition of 5 mM PEG-P(Glu)12-30 to prepare gadodiamide/DACHPt-encapsulating micelles. The resulting micelles were found to have an average particle size of 42 nm and a PdI of 0.174. In addition, 5 mM Gd-DTPA and 5 mM $CuCl_2$ were reacted, followed by addition of 5 mM PEG-P(Glu)12-30 to prepare Gd-DTPA/copper-encapsulating micelles. The resulting micelles were found to have an average particle size of 32.2 nm and a PdI of 0.158. Further, 5 mM iron acetylacetonate was dissolved in 50% DMF and mixed with 5 mM Gd-DTPA, immediately followed by addition of and reaction with 5 mM PEG-P(Glu)12-20 to prepare Gd-DTPA/iron-encapsulating micelles. The resulting micelles were found to have an average particle size of 23 to 110 nm and a PdI of 0.399.

Example 2

Figure 6:
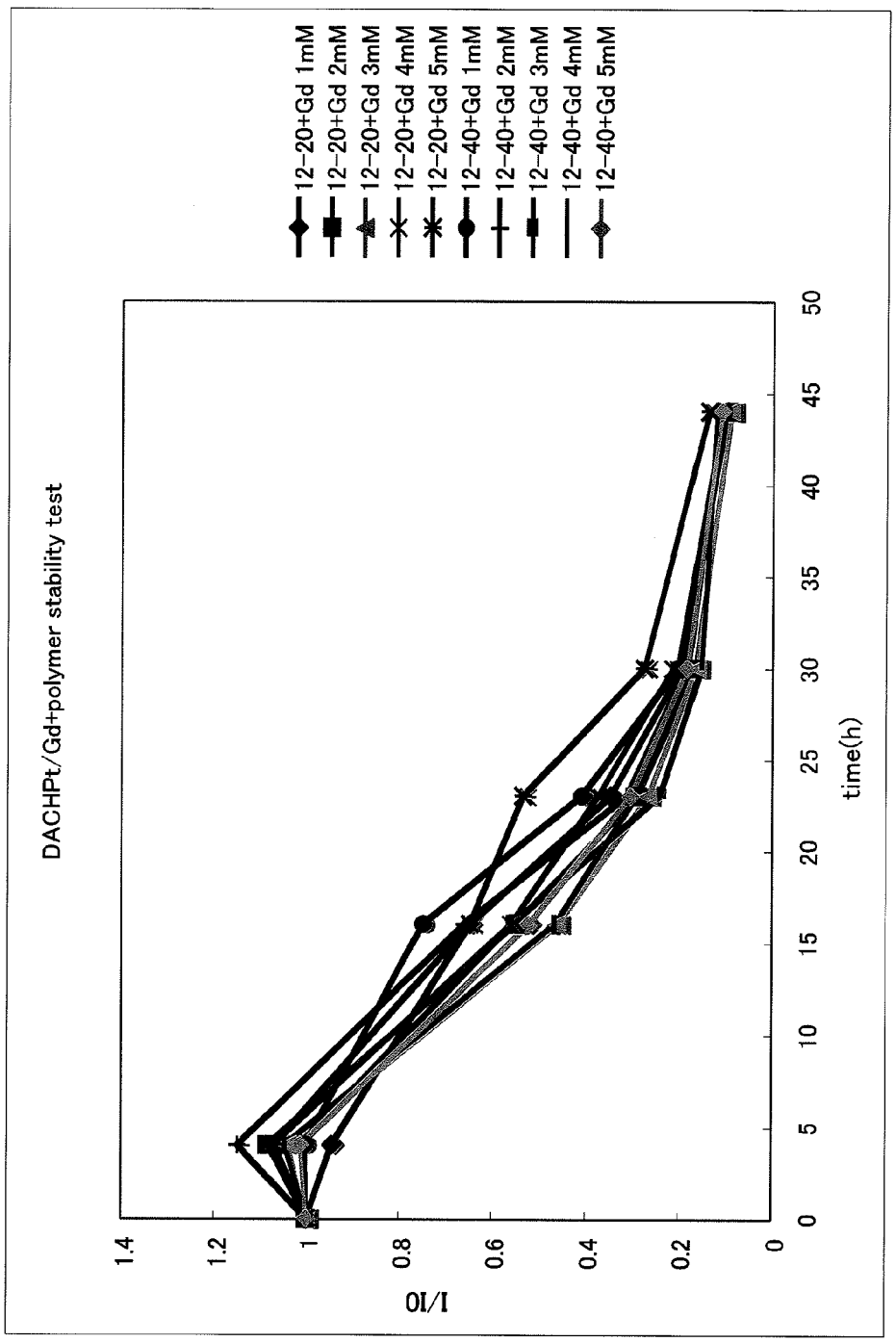
FIG. 6 is a graph showing the stability of micelles. All micelles showed substantially the same time-induced reduction in their intensity (scattered light intensity (I/I0); vertical axis in the graph). Although the micelles were gradually dissociated, 50% of the micelles were found to be able to remain in blood even 15 hours after administration.

The individual micelles prepared in Example 1 were evaluated for their stability in blood by measuring their scattered light intensity in a physiological environment. A fixed amount of micelles was mixed with pH 7.4, 10 mM PBS+150 mM NaCl and measured over time for their scattered light intensity (Zetasizer Nano ZS, Malvern Instruments) (FIG. 6). Simultaneously, the average particle size of the micelles was also measured over time by dynamic light scattering (Zetasizer Nano ZS, Malvern Instruments). As a result, although all of the micelles showed substantially the same time-induced reduction in their scattered light intensity (I/I0), they retained almost 50% of scattered light intensity even after 15 hours. This indicated that 50% of the micelles were able to remain in blood even 15 hours after drug administration.

In view of these results, the micelles used in the following experimental examples and examples were all prepared by using PEG-P(Glu)12-40 at a concentration of 5 mM (calculated as carboxylic acid), in combination with 5 mM Gd-DTPA and 5 mM DACHPt (Gd-DTPA/DACHPt-encapsulating micelles).

Figure 7:
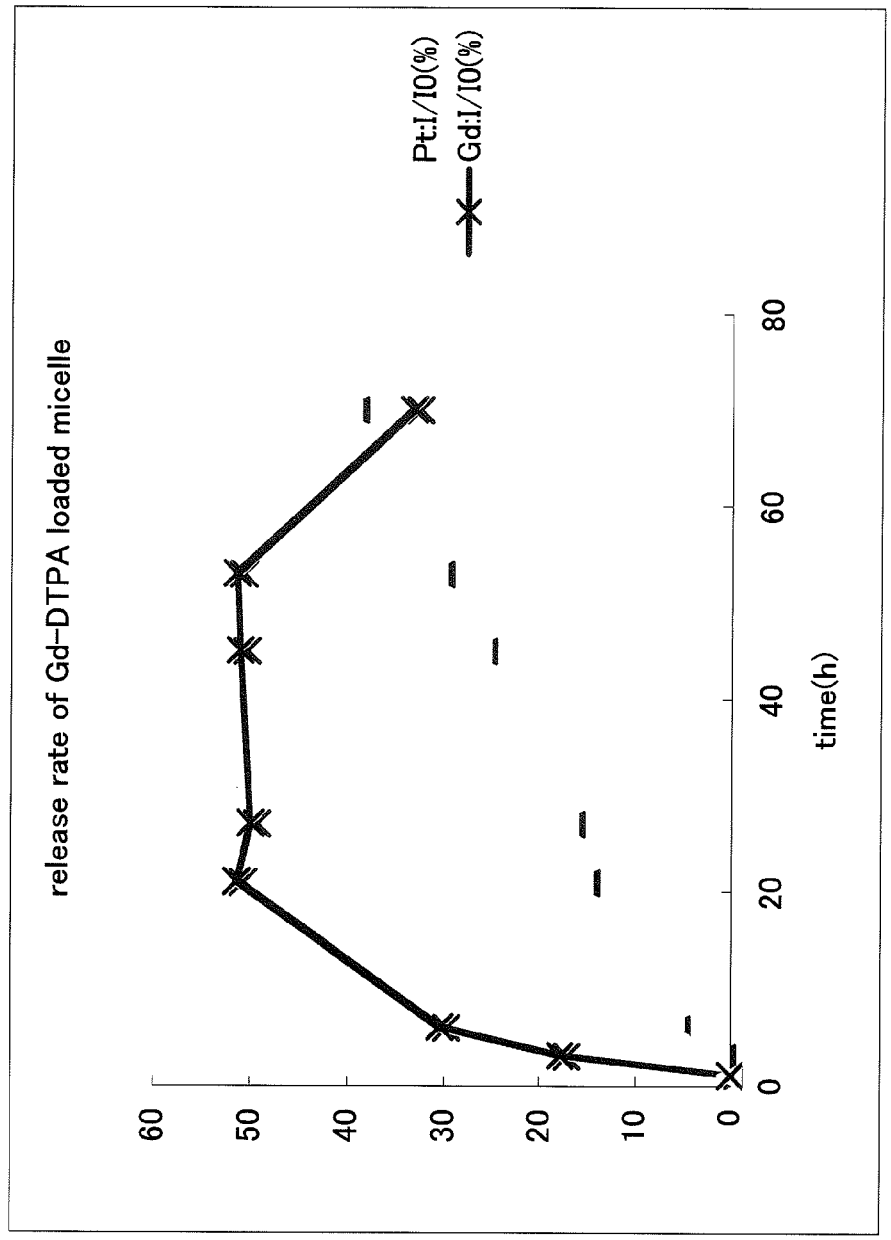
FIG. 7 is a graph showing drug release from micelles. This figure shows the release of both Gd and Pt from Gd-DTPA/DACHPt-encapsulating micelles. Pt was slowly released, whereas 50% of Gd was released within 20 hours.

The release behavior of drug (Gd-DTPA, DACHPt) from Gd-DTPA/DACHPt-encapsulating micelles was measured. More specifically, a 1 ml solution of 20 mM, pH 7.4 PBS+300 mM NaCl and a 1 ml solution of 2 mg/ml polymeric micelles were mixed and enclosed in a dialysis membrane with a MWCO of 6,000. This was transferred to a 99 ml solution of 10 mM, pH 7.4 PBS+150 mM NaCl, and the solution outside the dialysis membrane was sampled over time to analyze the amounts of Gd and Pt contained therein by ICP-MS. As a result, Gd was found to be released at a higher speed than Pt. 50% of Gd was released within 20 hours, whereas Pt was gradually released at a rate of 40% over 70 hours (FIG. 7).

Figure 8:
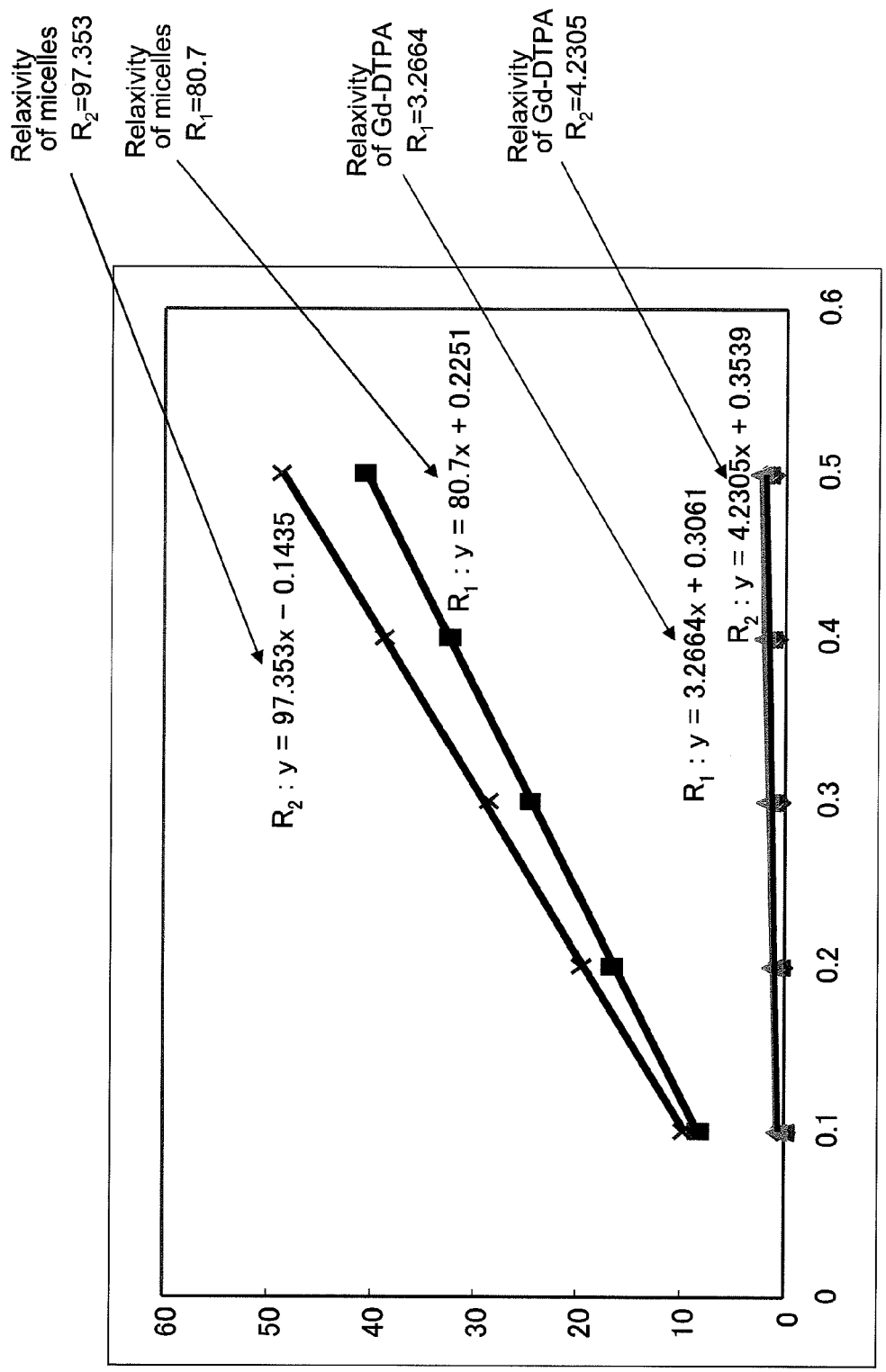
FIG. 8 is a graph showing the relaxivity of micelles. Gd-DTPA/DACHPt-encapsulating micelles were found to have relaxivity which was 20-fold or more higher than that of Gd-DTPA. It should be noted that the relaxivity is defined as follows: $1/T_1=1/T_{10}+R_1[Gd]$  $1/T_2=1/T_{20}+R_2[Gd]$  ($R_1$: $[mM^{-1} \cdot S^{-1}]$; $R_2$: $[mM^{-1} \cdot S^{-1}]$)

Parameters $R_1$ and $R_2$ were evaluated, which are indicative of MRI contrast agent sensitivity, i.e., relaxivity (contrast agent sensitivity). Higher relaxivity indicates higher sensitivity. First, samples to be measured were diluted with distilled water in a concentration range of 0.1 to 0.5 mM (calculated as Gd) and prepared as 1 ml solutions. Then, each sample was measured for $T_1$ and $T_2$ by the Inversion Recovery method and the Carr-Purcell-Meiboom-Gill method, respectively (JNM-MU25A, JEOL, Inc, 0.58T). Finally, the data were analyzed by preparing a graph whose x axis was the Gd concentration and whose y axis represented the reciprocals of $T_1$ and $T_2$, and then determining the relaxivity $R_1$ and $R_2$ from the respective slopes. As a result, the polymeric micelles were found to show 20-fold or more higher values than Gd-DTPA (FIG. 8). This indicates that the ability of the Gd-DTPA/DACHPt-encapsulating micelles as an MRI contrast agent is 20-fold or more higher than that of Gd-DTPA at the same Gd concentration.

Example 3

Figure 9:
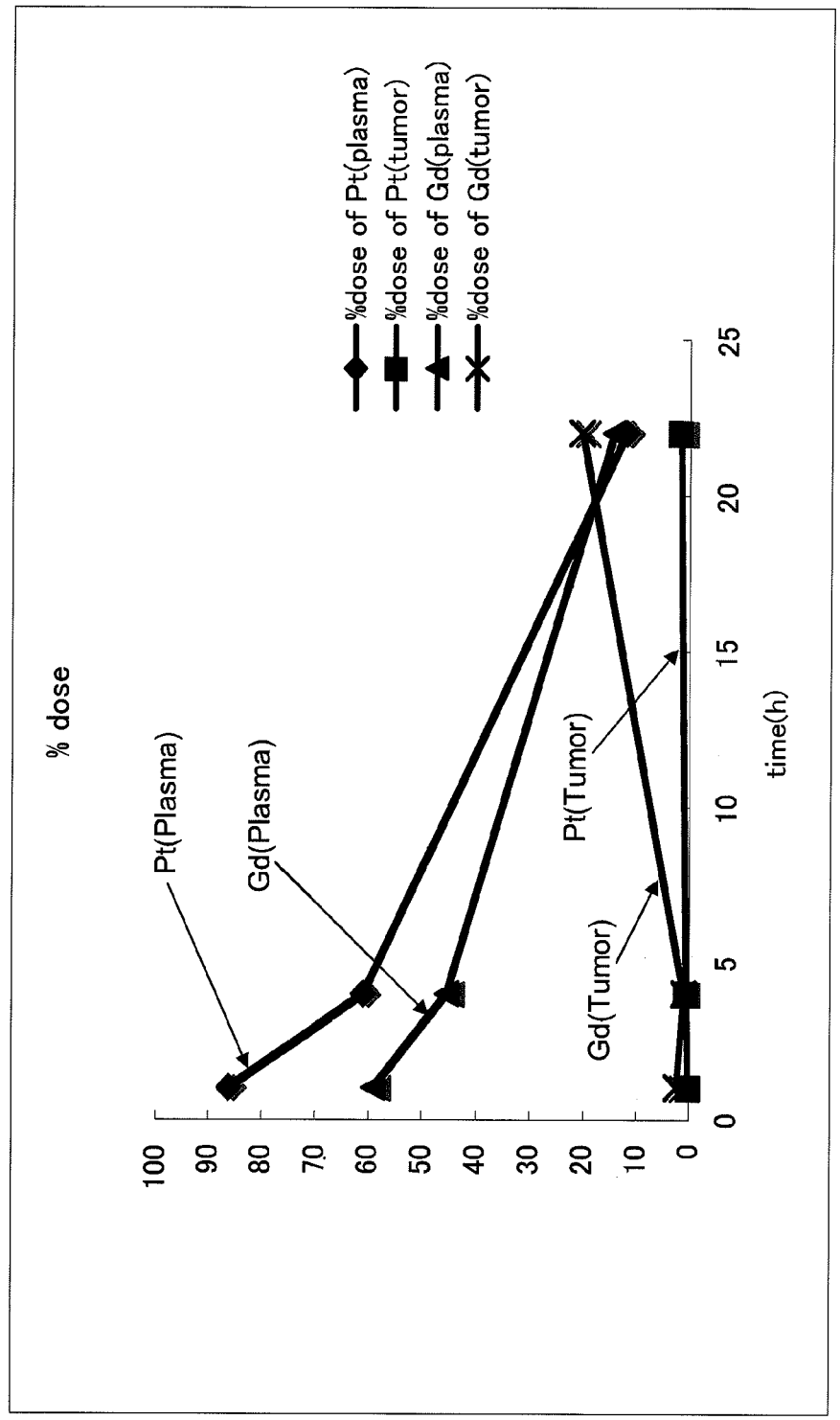
FIG. 9 is a graph showing the amounts (% dose) of Pt and Gd in plasma and in tumor at 1, 4 and 22 hours after injection of Gd-DTPA/DACHPt-encapsulating micelles.

With the aim of investigating the in vivo kinetics of the Gd-DTPA/DACHPt-encapsulating micelles, an in vivo experiment was conducted. CDF1 mice (female, 6 weeks of age) subcutaneously transplanted with C-26 colon cancer cells were each administered via the tail vein with the Gd-DTPA/DACHPt-encapsulating micelles, and after 1, 4 and 22 hours, tumor was excised from each mouse and 0.1 ml blood was collected via the inferior vena cava. To measure the concentrations of Gd and Pt contained in these tissues, each tissue was lysed with 90% $HNO_3$, dried by heating, dissolved in distilled water and then diluted, followed by ICP-MS to determine Gd and Pt contents in the resulting solution. FIG. 9 shows the amounts (% dose) of Pt and Gd in plasma and in tumor at 1, 4 and 22 hours after injection of the Gd-DTPA/DACHPt-encapsulating micelles. As a result, about 20% of Gd was found to be accumulated within tumor at 22 hours after injection, while Gd and Pt were each detected at a content of about 10% in plasma after 22 hours, indicating that the tested micelles had a high retention rate in blood, as in the case of conventional micelles (Japanese Patent No. 3955992).

Example 4

An in vivo MRI experiment was conducted using the Gd-DTPA/DACHPt-encapsulating micelles. CDF1 mice (female, 6 weeks of age) subcutaneously transplanted with C-26 colon cancer cells were used for imaging. MRI was imaged with a 4.7 Tesla Superconductive Magnet Unit (Varian, Palo Alto, Calif.) VXR-MRI Console under the following imaging conditions: repetition time (TR): 500 ms, echo time (TE): 15 ms, field of view (FOV): 32 mm×32 mm, matrix size: 128×128, slice thickness: 2 mm to obtain Spin Echo T1w images. The mice were injected under 5% isoflurane inhalation anesthesia and maintained under 1.2% isoflurane anesthesia during imaging. 0.2 ml of the Gd-DTPA/DACHPt-encapsulating micelles (Gd concentration: 500 µM) was injected via the tail vein, and each mice was fixed in the console. As a phantom control, a 1 ml syringe containing distilled water was also imaged. Imaging was performed every 5 minutes during the first 1 hour after injection via the tail vein, then every 15 minutes for 4 to 5 hours. Moreover, an equal amount of free Gd-DTPA serving as a control was also injected via the tail vein and imaged in the same manner.

The resulting images were analyzed by Mathematica (Wolfram Research Inc.) and Excel (Microsoft, Inc.).

The results indicated that the contrast enhancement in tumor was clearly higher than in Gd-DTPA, the signal intensity in tumor increased by 30% at 30 minutes after injection via the tail vein, and a positive contrast enhancement was obtained. Moreover, this contrast enhancement lasted for at least 4 hours (FIGS. 10 and 11).

Example 5

CDF1 mice (female, 6 weeks of age) subcutaneously transplanted with C-26 colon cancer cells were each administered via the tail vein with Gd-DTPA/DACHPt-encapsulating micelles or oxaliplatin (Free Ox) in a volume of 0.2 ml, and after 1, 4, 8 and 24 hours, 0.1 ml blood was collected via the inferior vena cava. Likewise, another group of the same mice were administered via the tail vein with the same micelles or Gd-DTPA (Free Gd-DTPA) in a volume of 0.2 ml, and after 1, 4, 8 and 24 hours, 0.1 ml blood was collected via the inferior vena cava. After collection, the blood was rapidly mixed with heparin to prevent coagulation, and then centrifuged to collect plasma only. The collected plasma was mixed with 90% HNO$_3$, heated and dried, dissolved in 5N HCl, and then diluted appropriately, followed by ICP-MS to determine Gd and Pt contents. The resulting values were divided by the drug amount initially administered to give % dose data, which were plotted in a graph (FIG. 12). This result indicated that the micelles increased the retention of both drugs in blood when compared to the free drugs.

Example 6

Nude mice (female, 6 weeks of age) subcutaneously transplanted with human pancreatic cancer cells (BxPC3) were intravenously injected with Gd-DTPA/DACHPt-encapsulating micelles (Pt content: 3 mg/ml) or oxaliplatin (Pt content: 8 mg/ml) in a volume of 0.2 ml on day 0, day 2 and day 4 (three times in total), and measured every 2 days starting from day 0 for their tumor size (major axis=a cm, minor axis=b cm; a×b$^2$=approximate value of tumor volume) and their body weight, which were compared with those measured for the control group (n=6).

The Gd-DTPA/DACHPt-encapsulating micelles showed a sufficient antitumor effect even at a Pt content of 3 mg/ml, whereas oxaliplatin showed substantially the same tendency as the control even at a Pt content of 8 mg/ml. Thus, the micelles were also proven to have an anticancer effect against pancreatic cancer (FIG. 13, left). Moreover, there was little reduction in body weight, suggesting that the micelles had no serious side effect (FIG. 13, right).

Example 7

Nude mice (female, 6 weeks of age) were laparotomized under inhalation anesthesia, injected with 0.1 ml of human pancreatic cancer cells (BxPC3) under the serous membrane of the pancreas and then kept for 1 month to prepare an orthotopic transplantation model. MRI was imaged with a 4.7 Tesla Superconductive Magnet Unit (Varian, Palo Alto, Calif.) VXR-MRI Console under the following imaging conditions: repetition time (TR): 500 ms, echo time (TE): 15 ms, field of view (FOV): 32 mm×32 mm, matrix size: 256×256, slice thickness: 2 mm to obtain Spin Echo T1w images. The mice were injected under 5% isoflurane inhalation anesthesia and maintained under 1.2% isoflurane anesthesia during imaging. 0.2 ml of Gd-DTPA/DACHPt-encapsulating micelles (Gd concentration: 500 µM) was injected via the tail vein, and each mice was fixed in the console. Imaging was performed every 5 minutes during the first 1 hour after injection via the tail vein, then every 15 minutes for 4 hours. Moreover, an equal amount of free Gd-DTPA serving as a control was also injected via the tail vein and imaged in the same manner.

The resulting images were analyzed by Mathematica (Wolfram Research Inc.) and Excel (Microsoft, Inc.).

The results indicated that the contrast enhancement in tumor was clearly higher in the Gd-DTPA/DACHPt-encapsulating micelles than in Gd-DTPA, the increase in intensity reached up to 200%, and further the contrast enhancement lasted for at least 4 hours. In contrast, other organs (liver, kidney, spleen) showed a slight increase in intensity, but the drug was washed out from these organs, so that the contrast enhancement remained only in tumor (FIGS. 14 and 15).

INDUSTRIAL APPLICABILITY

The present invention enables the provision of a polymer-metal complex composite which comprises a block copolymer capable of serving as a constituent member of a polymeric micelle and a metal complex having MRI contrast ability, wherein the composite accumulates in a tumor-specific manner, achieves high image contrast even in a small amount, and has reduced side effects and a long retention time in blood. The present invention further enables the provision of an MRI contrasting (and/or antitumor) composition or kit which comprises such a composite, as well as an MRI contrasting method for tumor detection which uses such a composite.

The invention claimed is:

1. A polymer-metal complex composite, which comprises a block represented by the following general formula (1) or (2):

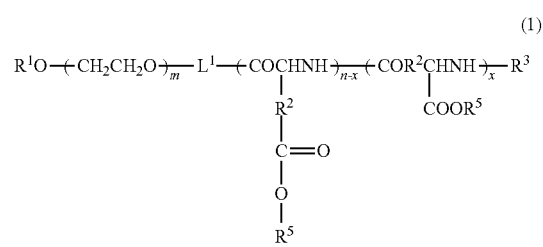

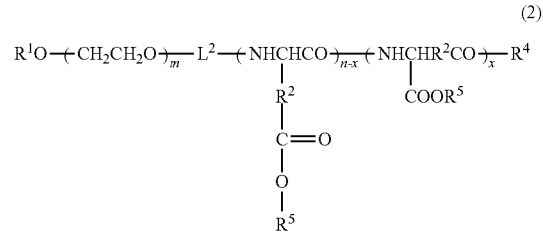

wherein R$^1$ represents a hydrogen atom or an unsubstituted or substituted linear or branched C$_{1-12}$ alkyl group, L$^1$ and L$^2$ each represent a linker group, R$^2$ independently represents a methylene group or an ethylene group, R$^3$ independently represents a hydrogen atom, a protecting group for an amino group, a hydrophobic group or a polymerizable group, R$^4$ represents a hydroxyl group or an initiator residue, R$^5$ independently represents a hydrogen atom, an alkali metal ion, or a group represented by the following general formula (3) and/or (4):

wherein R$^6$ represents a metal atom or a group derived from a metal complex, and R$^7$ represents a group derived from a metal complex having MRI contrast ability, provided that at least one R$^5$ comprises the group represented by general formula (3) in which each R$^6$ is independently a group derived from a metal complex having antitumor activity represented by the following formula (5-a) or (6-a):

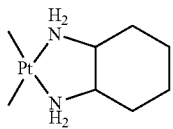

(5-a)

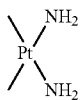

(6-a)

each $R^7$ is independently a group represented by the following formula (7-a), (8-a), (9-a) or (10-a):

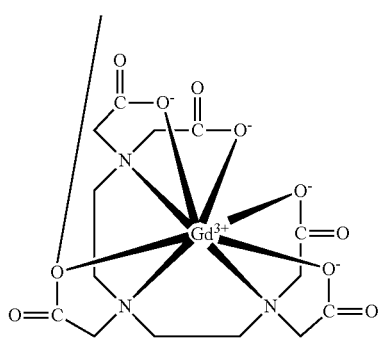

(7-a)

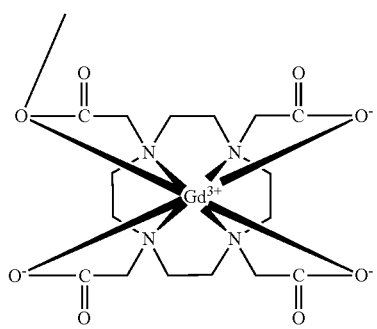

(8-a)

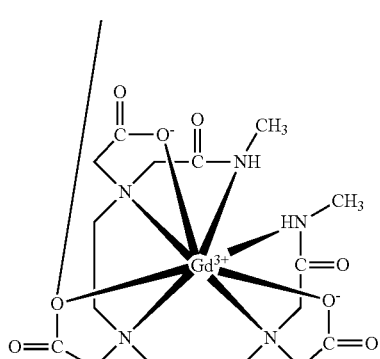

(9-a)

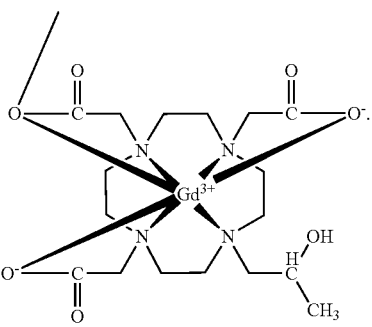

(10-a)

m represents an integer of 5 to 20,000, n represents an integer of 2 to 5,000, and x represents an integer of 0 to 5,000 provided that $x \leq n$.

2. The composite according to claim 1, which is represented by the following general formula (1-a) or (2-a):

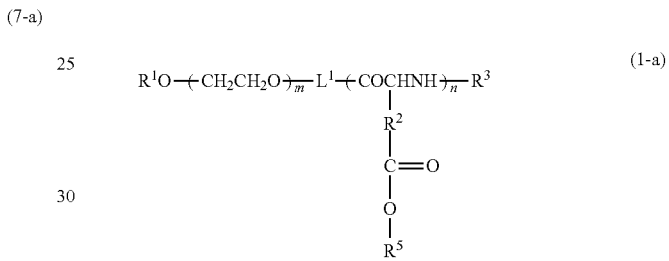

(1-a)

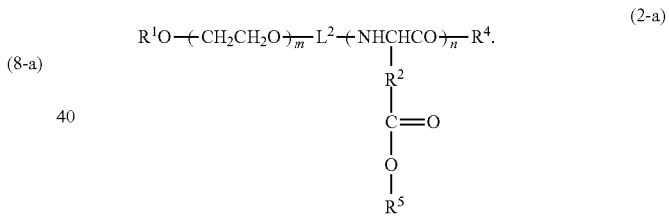

(2-a)

3. The composite according to claim 1 or 2, wherein the group represented by general formula (3) is independently a group represented by the following formula (15-a), (16-a), (17-a) or (18-a):

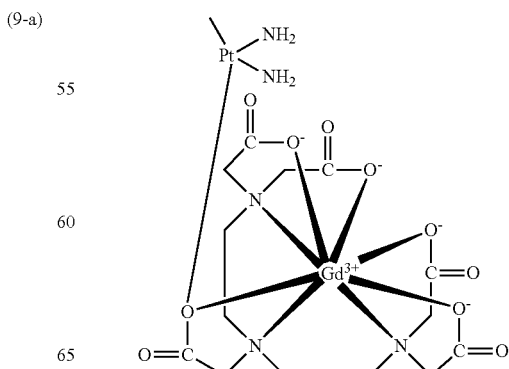

-continued

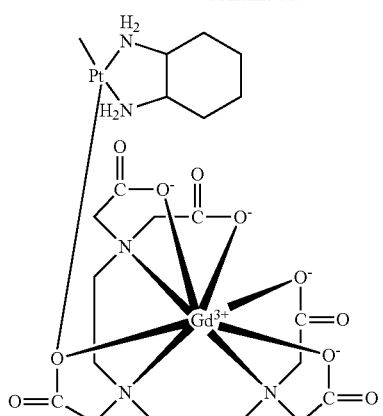

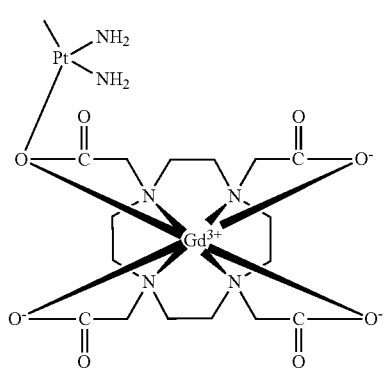

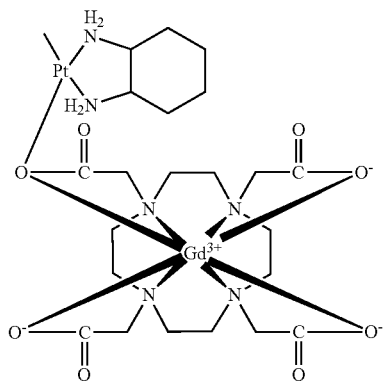

(15-a)

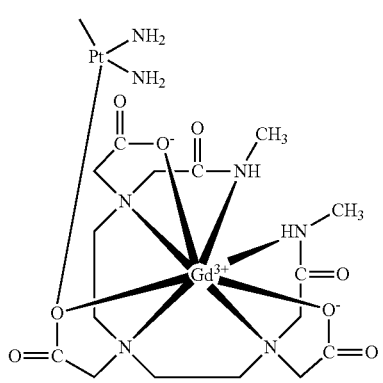

-continued (16-a)

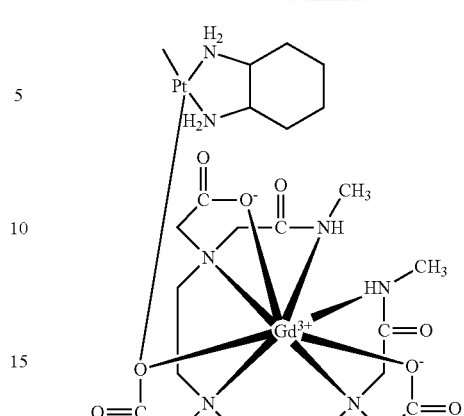

(17-a)

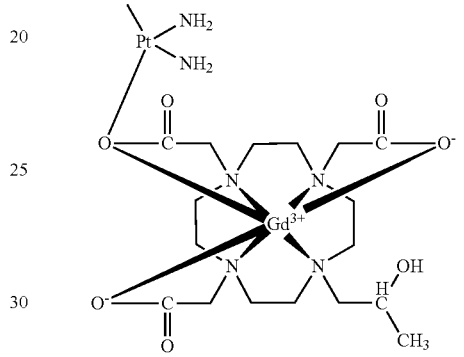

(18-a)

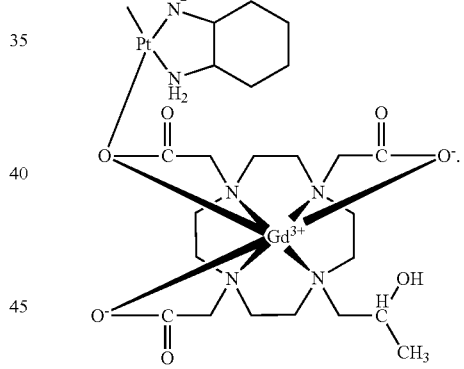

4. The composite according to claim 1, which when dispersed in an aqueous medium forms micellar particles.

5. The composite according to claim 4, which has an average dispersed particle size of 10 nm to 1 μm in an aqueous medium, as measured by dynamic light scattering.

6. An MRI contrasting and antitumor composition, which comprises the composite according to claim 1.

7. An MRI contrasting method for tumor detection, which comprises administering the composite according to claim 1 to the body of an animal subject.

8. An MRI contrasting and antitumor kit, which comprises the composite according to claim 1.

9. The composite according to claim 1 or 2, wherein the group represented by general formula (3) is independently a group represented by the following formula (11-a), (12-a), (13-a), or (14-a):

(11-a)
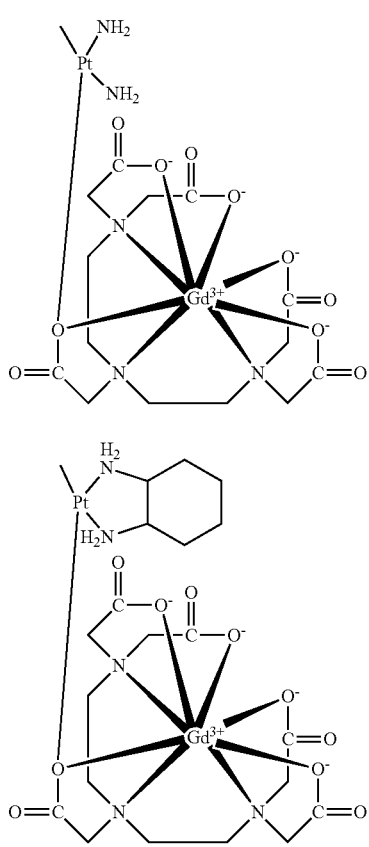
(12-a)
(13-a)
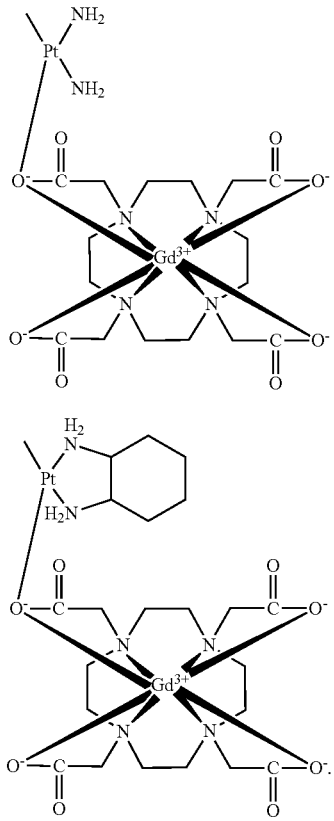
(14-a)
* * * * *